US012694579B2

(12) United States Patent
Shaked et al.

(10) Patent No.: US 12,694,579 B2
(45) Date of Patent: Jul. 28, 2026

(54) MEDICAL IMAGE PRIVACY PRESERVATION VIA IMAGE SYNTHESIS AND FILTRATION

(71) Applicant: GE Precision Healthcare LLC, Waukesha, WI (US)

(72) Inventors: Doron Shaked, Tivon (IL); Amitay Lev, Or Akiva (IL); Uriel Cohen, Haifa (IL); Hannah Michele Ornstein, Haifa (IL); Elay Dahan, Haifa (IL); Chandan Kumar Mallappa Aladahalli, Bengaluru (IN); Gopal Biligeri Avinash, Concord, CA (US)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 249 days.

(21) Appl. No.: 18/669,884

(22) Filed: May 21, 2024

(65) Prior Publication Data

US 2025/0364115 A1     Nov. 27, 2025

(51) Int. Cl.
| | |
|---|---|
| *G16H 30/20* | (2018.01) |
| *G06T 11/60* | (2006.01) |
| *G06V 10/25* | (2022.01) |
| *G06V 10/764* | (2022.01) |
| *G06V 10/82* | (2022.01) |
| (Continued) | |

(52) U.S. Cl.
CPC ............. *G16H 30/20* (2018.01); *G06T 11/60* (2013.01); *G06V 10/25* (2022.01); *G06V 10/764* (2022.01); *G06V 10/82* (2022.01); *G16H 30/40* (2018.01); *G06V 2201/07* (2022.01); *H04N 1/387* (2013.01)

(58) Field of Classification Search
None
See application file for complete search history.

(56) References Cited

U.S. PATENT DOCUMENTS

| | | | |
|---|---|---|---|
| 11,901,064 | B2 * | 2/2024 | Ceballos Lentini .. G06T 7/0012 |
| 2020/0226752 | A1 * | 7/2020 | Lee ........................... G06T 5/60 |
| | | (Continued) | |

FOREIGN PATENT DOCUMENTS

| | | |
|---|---|---|
| EP | 4057292 A1 | 9/2022 |

OTHER PUBLICATIONS

Kulikov, et al. "SinDDM: A Single Image Denoising Diffusion Model" arXiv:2211.16582v3 [cs.CV] Jun. 6, 2023, 39 pages.

(Continued)

*Primary Examiner* — Haris Sabah
(74) *Attorney, Agent, or Firm* — Amin, Turocy & Watson, LLP

(57) ABSTRACT

Systems or techniques that facilitate medical image privacy preservation via image synthesis and filtration are provided. In various embodiments, a system can access a medical image for which a first artificial neural network has produced an inferencing task result. In various aspects, the system can train a second artificial neural network on the medical image to perform image synthesis. In various instances, the system can generate, via execution of the second artificial neural network post-training, a set of synthetic variants of the medical image. In various cases, the system can fine-tune the first artificial neural network using at least some of the set of synthetic variants of the medical image rather than using the medical image.

20 Claims, 13 Drawing Sheets

(51) Int. Cl.
    *G16H 30/40*       (2018.01)
    *H04N 1/387*     (2006.01)

(56)           References Cited

U.S. PATENT DOCUMENTS

| | | | | |
|---|---|---|---|---|
| 2020/0311913 | A1* | 10/2020 | Soni | G16H 50/20 |
| 2020/0311932 | A1* | 10/2020 | Hooper | G06F 18/2413 |
| 2021/0035287 | A1* | 2/2021 | Kim | G06T 7/0012 |
| 2021/0233239 | A1* | 7/2021 | Li | G16H 30/40 |
| 2021/0279869 | A1 | 9/2021 | Soni | |
| 2022/0180447 | A1 | 6/2022 | Kearney | |

OTHER PUBLICATIONS

Nikankin, et al. "SinFusion: Training Diffusion Models on a Single Image or Video", arXiv:2211.11743v3 [cs.CV] Jun. 19, 2023, 16 pages.

Alexander Chebykin et al, "Hyperparameter-Free Medical Image Synthesis for Sharing Data and Improving Site-Specific Segmentation", arxiv.org, Cornell University Library, 201 Olin Library Cornell University Ithaca, NY 14853, Apr. 9, 2024 (Apr. 9, 2024), XP091723550, Sections 3.1, 3 .5; 22 pages.

Fernandez Virginia et al, "Privacy Distillation: Reducing Re-identification Risk of Diffusion Models", Feb. 20, 2024 (Feb. 20, 2024), Deep Generative Models; [Lecture Notes in Computer Science; Lect.Notes Computer], Springer Nature Switzerland, Cham, pp. 3-13, XP047680581, ISSN: 0302-9743 ISBN: 978-3-031-53766-0, [retrieved on Feb. 20, 2024] Section 2.3 12 pages.

Yuan Xue et al: "Selective Synthetic Augmentation with HistoGAN for Improved Histopathology Image Classification", arxiv.org, Cornell University Library, 201 Olin Library Cornell University Ithaca, NY 14853, Nov. 10, 2021 (Nov. 10, 2021), XP091096219, DOI: 10.1016/ J.MEDIA.2020.101816, Section 3.2; 16 pages.

International Application No. PCT/US2025/026904 filed on Apr. 29, 2025, International Search Report and Written Opinion issued Jul. 29, 2025, 16 pages.

* cited by examiner

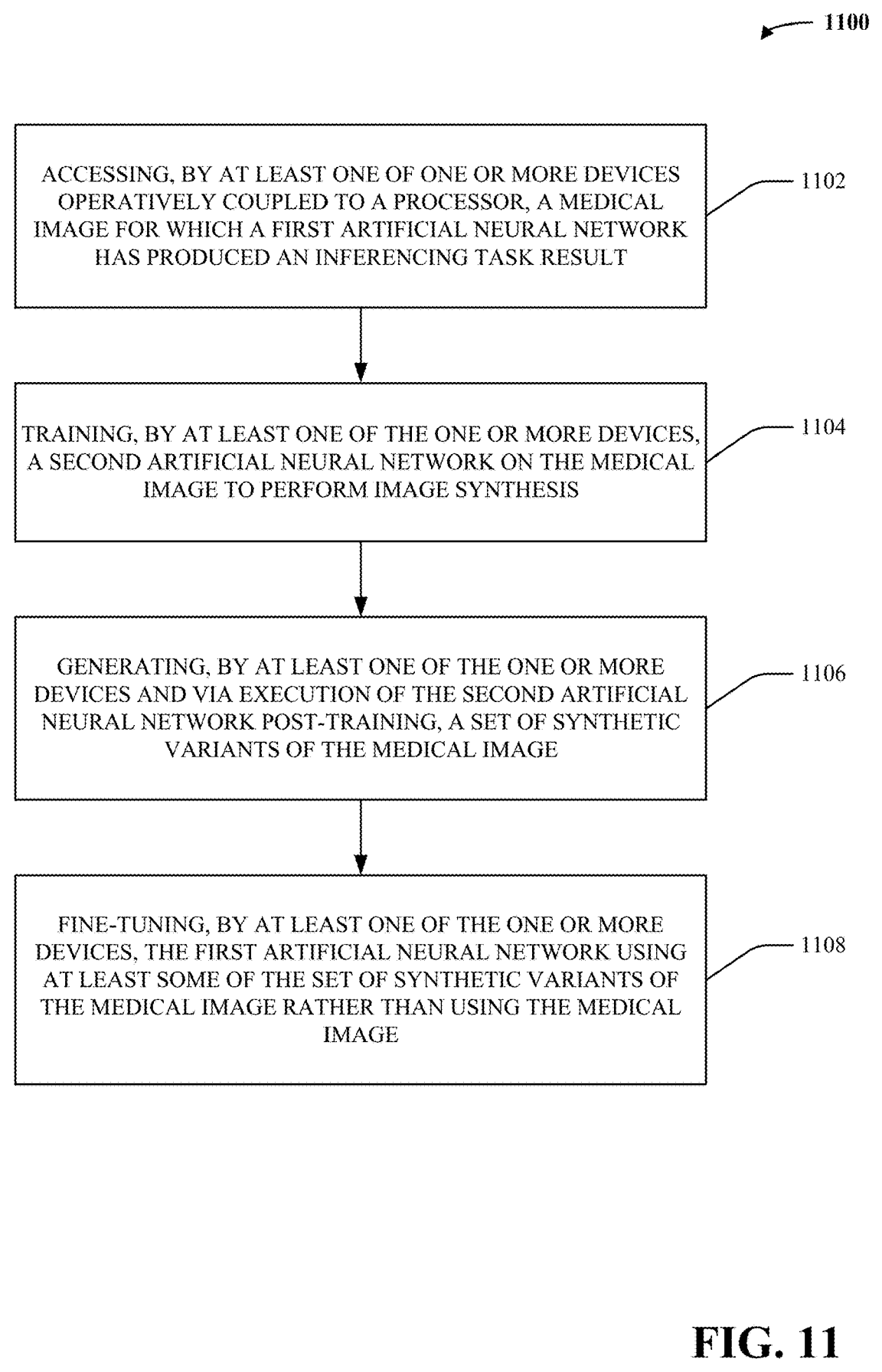

— 1100

ACCESSING, BY AT LEAST ONE OF ONE OR MORE DEVICES OPERATIVELY COUPLED TO A PROCESSOR, A MEDICAL IMAGE FOR WHICH A FIRST ARTIFICIAL NEURAL NETWORK HAS PRODUCED AN INFERENCING TASK RESULT — 1102

TRAINING, BY AT LEAST ONE OF THE ONE OR MORE DEVICES, A SECOND ARTIFICIAL NEURAL NETWORK ON THE MEDICAL IMAGE TO PERFORM IMAGE SYNTHESIS — 1104

GENERATING, BY AT LEAST ONE OF THE ONE OR MORE DEVICES AND VIA EXECUTION OF THE SECOND ARTIFICIAL NEURAL NETWORK POST-TRAINING, A SET OF SYNTHETIC VARIANTS OF THE MEDICAL IMAGE — 1106

FINE-TUNING, BY AT LEAST ONE OF THE ONE OR MORE DEVICES, THE FIRST ARTIFICIAL NEURAL NETWORK USING AT LEAST SOME OF THE SET OF SYNTHETIC VARIANTS OF THE MEDICAL IMAGE RATHER THAN USING THE MEDICAL IMAGE — 1108

FIG. 11

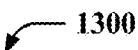
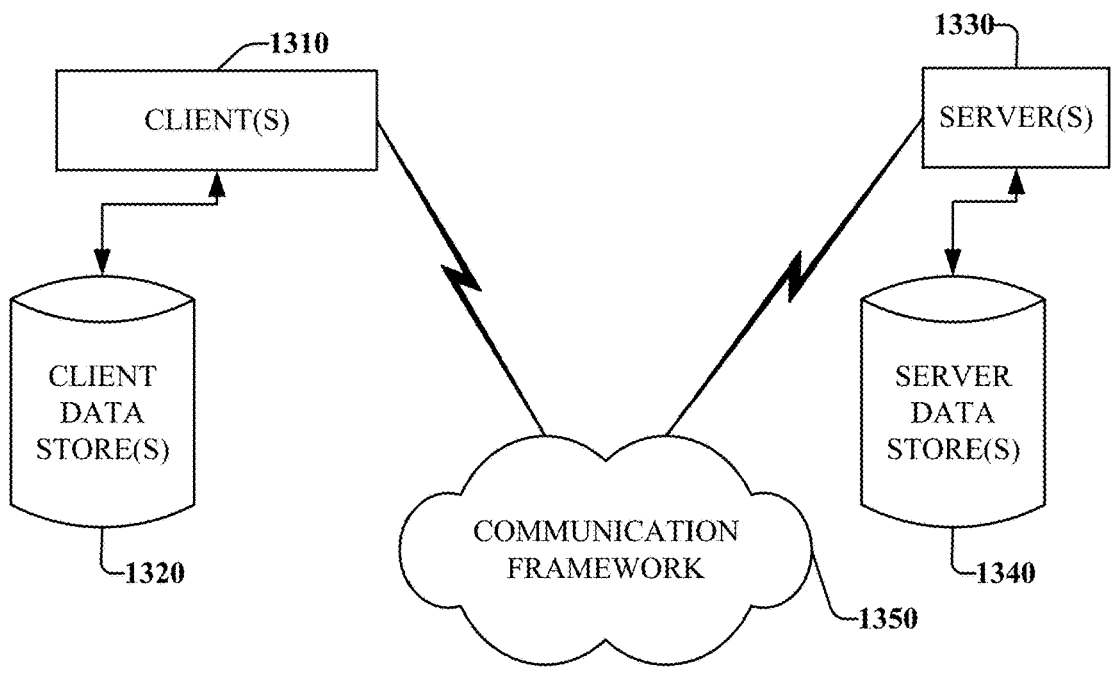
FIG. 13

MEDICAL IMAGE PRIVACY PRESERVATION VIA IMAGE SYNTHESIS AND FILTRATION

TECHNICAL FIELD

The subject disclosure relates generally to machine learning, and more specifically to medical image privacy preservation via image synthesis and filtration.

BACKGROUND

A deep learning neural network can be trained to perform an inferencing task on inputted medical images. After being trained, the deep learning neural network can be deployed in the field, so as to perform the inferencing task on inputted medical images. To maintain the deep learning neural network's performance over time during such deployment, continual learning can be applied to the deep learning neural network. However, continual learning can be efficacious only when driven by realistic training images. Unfortunately, real-world medical images are often subject to privacy restrictions and thus are often not available for continual learning.

Accordingly, systems or techniques that can address one or more of these technical problems can be desirable.

SUMMARY

The following presents a summary to provide a basic understanding of one or more embodiments. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, devices, systems, computer-implemented methods, apparatus or computer program products that facilitate medical image privacy preservation via image synthesis and filtration are described.

According to one or more embodiments, a system is provided. The system can comprise a non-transitory computer-readable memory that can store computer-executable components. The system can further comprise a processor that can be operably coupled to the non-transitory computer-readable memory and that can execute the computer-executable components stored in the non-transitory computer-readable memory. In various embodiments, the computer-executable components can comprise an access component that can access a medical image on which a first artificial neural network has been executed. In various aspects, the computer-executable components can comprise a synthesis component that: can train a second artificial neural network on the medical image to perform image synthesis; and can generate, via execution of the second artificial neural network post-training, a set of synthetic variants of the medical image. In various instances, the computer-executable components can comprise a fine-tune component that can instruct a computing device to fine-tune the first artificial neural network using at least some of the set of synthetic variants of the medical image rather than using the medical image.

According to one or more embodiments, a computer-implemented method is provided. In various embodiments, the computer-implemented method can comprise accessing, by at least one of one or more devices operatively coupled to a processor, a medical image on which a first artificial neural network has been executed. In various aspects, the computer-implemented method can comprise training, by at least one of the one or more devices, a second artificial neural network on the medical image to perform image synthesis. In various instances, the computer-implemented method can comprise generating, by at least one of the one or more devices and via execution of the second artificial neural network post-training, a set of synthetic variants of the medical image. In various cases, the computer-implemented method can comprise instructing, by at least one of the one or more devices, a computing device to fine-tune the first artificial neural network using at least some of the set of synthetic variants of the medical image rather than using the medical image.

According to one or more embodiments, a computer program product for facilitating medical image privacy preservation via image synthesis and filtration is provided. In various embodiments, the computer program product can comprise a non-transitory computer-readable memory having program instructions embodied therewith. In various aspects, the program instructions can be executable by a processor to cause the processor to access a privacy-restricted medical image which a clinical machine learning model has analyzed. In various instances, the program instructions can be further executable to cause the processor to generate, via execution of a generative model that is trained on the privacy-restricted medical image to perform image synthesis, a set of unrestricted synthetic variants of the privacy-restricted medical image. In various cases, the program instructions can be further executable to cause the processor to retrain the clinical machine learning model using at least some of the set of unrestricted synthetic variants instead of the privacy-restricted medical image.

DESCRIPTION OF THE DRAWINGS

FIG. 11 illustrates a flow diagram of an example, non-limiting computer-implemented method that facilitates medical image privacy preservation via image synthesis and filtration in accordance with one or more embodiments described herein.

FIG. 13 illustrates an example networking environment operable to execute various implementations described herein.

DETAILED DESCRIPTION

Figure 1:
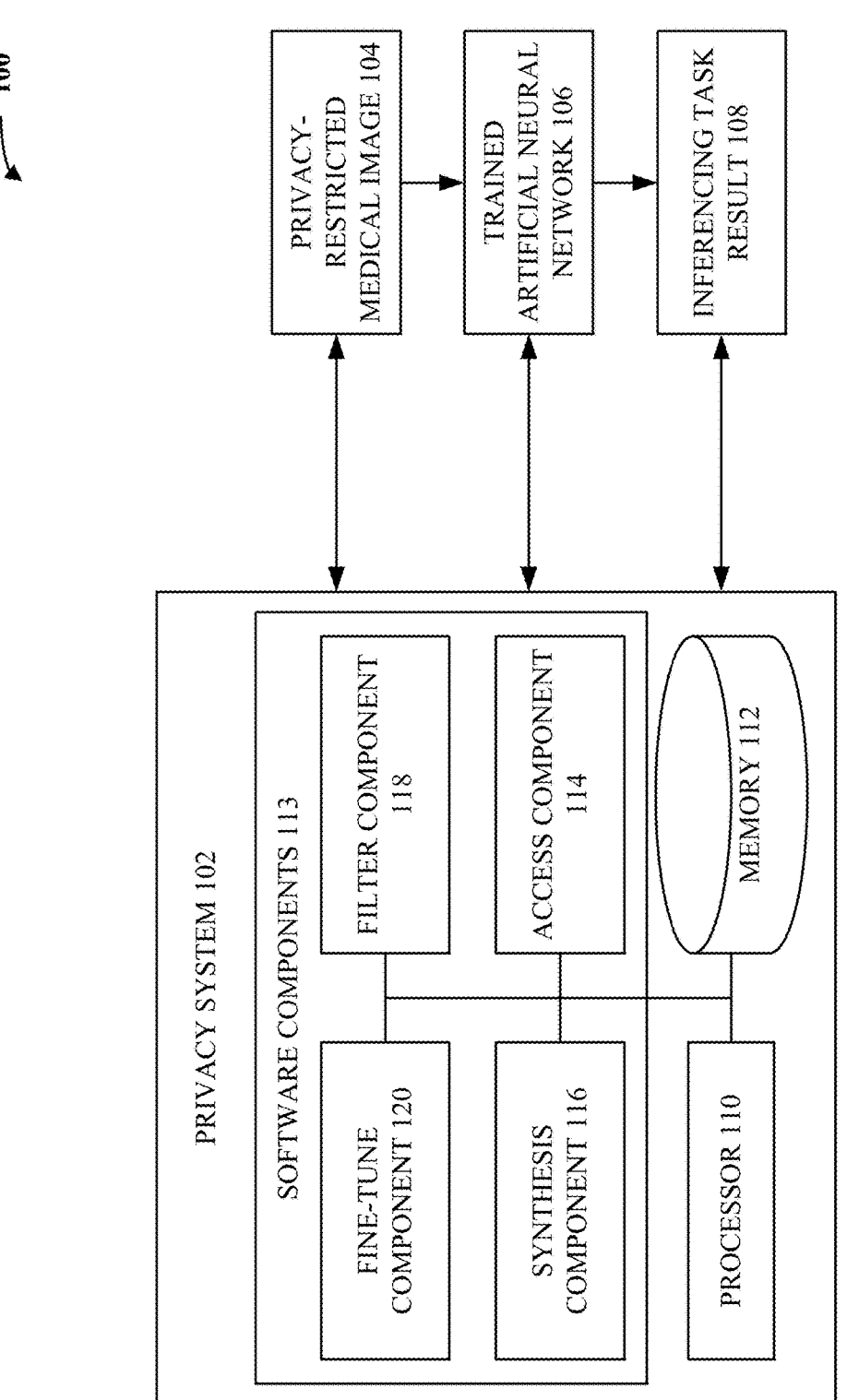
FIG. 1 illustrates a block diagram of an example, non-limiting system that facilitates medical image privacy preservation via image synthesis and filtration in accordance with one or more embodiments described herein.

The following detailed description is merely illustrative and is not intended to limit embodiments or application/uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

A deep learning neural network can be trained (e.g., in supervised fashion, in unsupervised fashion, in reinforcement learning fashion) to perform an inferencing task (e.g., classification, segmentation, regression) on inputted medical images. After being trained, the deep learning neural network can be deployed in the field, so as to perform the inferencing task on inputted medical images. For example, the deep learning neural network can generate classification labels, segmentation masks, or regression results for real-world medical images that are captured or generated by real-world medical imaging equipment (e.g., by computed tomography (CT) scanners, by magnetic resonance imaging (MRI) scanners, by X-ray scanners, by ultrasound scanners, by positron emission tomography (PET) scanners, by nuclear medicine (NM) scanners), and those classification labels, segmentation masks, or regression results can be leveraged to provide diagnoses or prognoses for real-world medical patients (e.g., humans, animals, or otherwise).

To maintain the deep learning neural network's performance over time during such deployment, continual learning can be applied to the deep learning neural network. That is, feedback (e.g., provided by medical professionals) regarding how well or how poorly the deep learning neural network is analyzing whatever medical images it encounters during deployment can be regularly obtained, and the deep learning neural network can be regularly re-trained or fine-tuned using such feedback. In other words, the deep learning neural network can be monitored during deployment, and the observations of such monitoring can be used to help preserve or improve the inferencing behavior of the deep learning neural network. Such continual learning can help to prevent the deep learning neural network from succumbing to the problem of data drift or clinical interpretation drift. Indeed, characteristics or properties of the medical images that the deep learning neural network encounters during deployment can drift or become too different from those of the medical images on which the deep learning neural network was trained, and the deep learning neural network cannot be expected to accurately or reliably analyze drifted medical images. So, continual or regular re-training or fine-tuning can keep the deep learning neural network up-to-date with such drifted medical images, thereby preserving or improving inferencing accuracy.

However, continual learning can be efficacious only when driven by realistic medical images. Unfortunately, real-world medical images associated with real-world medical patients are often subject to privacy restrictions that prohibit them from being available for continual learning. For example, various governmental jurisdictions and entities have imposed privacy laws or regulations that stipulate that medical images constitute private healthcare information that cannot be shared without patient consent. This can be problematic in situations where the device that deploys the deep learning neural network is not necessarily the same device that trains or re-trains the deep learning neural network. Indeed, it can often be the case that the deep learning neural network is: constructed, built, trained, or re-trained using computerized devices of a software development company; but deployed or utilized for medical diagnoses or prognoses by computerized devices of a hospital or clinic. Accordingly, the computerized devices of the hospital or clinic may have permission to capture (e.g., via medical imaging scanners) real-world medical images of patients and to analyze those real-world medical images by executing the deep learning neural network, but the computerized devices of the hospital or clinic may lack permission to share or transfer those real-world medical images to the computerized devices of the software development company. Accordingly, those real-world medical images can be considered as unavailable for continual learning.

So, systems or techniques that can address one or more of these technical problems can be desirable.

Various embodiments described herein can address one or more of these technical problems. One or more embodiments described herein can include systems, computer-implemented methods, apparatus, or computer program products that can facilitate medical image privacy preservation via image synthesis and filtration. In particular, when given any privacy-restricted medical image on which it is desired to re-train or fine-tune a first deep learning neural network, various embodiments described herein can involve training an image synthesizer to receive as input random arrays and to produce as output synthetic images that resemble the given privacy-restricted medical image. Accordingly, the image synthesizer can be executed on various random arrays, thereby producing various synthetic versions of the given privacy-restricted medical image. Note that, because random arrays can have different numerical elements than each other, the various synthetic versions of the given privacy-restricted medical image can likewise have different visual characteristics or contents than each other and thus than the given privacy-restricted medical image (e.g., synthetic versions can have uniquely additional, missing, or distorted visual objects or artifacts than the given privacy-restricted medical image). In various cases, the various synthetic versions can be filtered as described herein (e.g., filtered according to respective anatomical content; filtered according to respective embedded representations; filtered according to respective inferencing task results or hidden activation maps produced by the deep learning neural network). In various instances, such filtration can help to ensure that the various synthetic versions are visually similar enough to the given privacy-restricted medical image so as to be useful in continual learning while simultaneously being visually different enough from the given privacy-restricted medical image so as to not violate privacy laws or regulations. Thus, the various filtered synthetic versions can be leveraged to re-train or fine-tune the deep learning neural network, rather than the given privacy-restricted medical image (e.g., the deep learning neural network can learn how to handle the underlying visual substance of the given privacy-restricted medical image, without violating the privacy laws or regulations that apply to the given privacy-restricted medical image).

Various embodiments described herein can be considered as a computerized tool (e.g., any suitable combination of computer-executable hardware or computer-executable software) that can facilitate medical image privacy preservation via image synthesis and filtration. In various aspects, such computerized tool can comprise an access component, a synthesis component, a filter component, or a fine-tune component.

In various embodiments, there can be a first deep learning neural network. In various aspects, the first deep learning neural network can exhibit any suitable deep learning internal architecture. For example, the first deep learning neural network can include any suitable numbers of any suitable types of layers (e.g., input layer, one or more hidden layers, output layer, any of which can be convolutional layers, dense layers, long short-term memory (LSTM) layers, transformer layers, non-linearity layers, pooling layers, batch normalization layers, or padding layers). As another example, the first deep learning neural network can include any suitable numbers of neurons in various layers (e.g., different layers can have the same or different numbers of neurons as each other). As yet another example, the first deep learning neural network can include any suitable activation functions (e.g., softmax, sigmoid, hyperbolic tangent, rectified linear unit) in various neurons (e.g., different neurons can have the same or different activation functions as each other). As still another example, the first deep learning neural network can include any suitable interneuron connections or interlayer connections (e.g., forward connections, skip connections, recurrent connections).

Regardless of its internal architecture, the first deep learning neural network can be configured to perform an inferencing task on any suitable inputted images. In various aspects, the first deep learning neural network can be configured to operate on images having any suitable format, size, or dimensionality (e.g., can be configured to operate on two-dimensional pixel arrays, or can be configured to operate on three-dimensional voxel arrays). In various instances, the first deep learning neural network can be configured to operate on images that are captured or generated by any suitable imaging modality (e.g., by a CT scanner, by an MRI scanner, by an X-ray scanner, by an ultrasound scanner, by a PET scanner, by an NM scanner). In various instances, the inferencing task can be any suitable computational, predictive task that can be performed on or with respect to an image. As some non-limiting examples, the inferencing task can be image classification (e.g., classifying or diagnosing a pathology depicted in a medical image), image segmentation (e.g., localizing the boundary of an anatomical structure or surgical implant depicted in a medical image), or image regression (e.g., denoising or enhancing resolution of a medical image, so as to aid diagnosis).

In various embodiments, the first deep learning neural network can be trained in any suitable fashion (e.g., in supervised fashion, in unsupervised fashion, in reinforcement learning fashion) on an original training dataset to perform the inferencing task. In various aspects, the original training dataset can comprise any suitable number of training images. In various instances, a training image can be any suitable image on which the first deep learning neural network can be executed (e.g., if the first deep learning neural network is configured to operate on two-dimensional pixel arrays captured by CT scanners, then a training image can be a two-dimensional pixel array captured by a CT scanner; if the first deep learning neural network is instead configured to operate on three-dimensional voxel arrays captured by MRI scanners, then a training image can instead be a three-dimensional voxel array captured by an MRI scanner). In various cases, the original training dataset can be unannotated (e.g., in such case, the first deep learning neural network can be trained in unsupervised or reinforcement learning fashion on the original training dataset). In other cases, however, the original training dataset can be annotated (e.g., in such case, the first deep learning neural network can be trained on the original training dataset in supervised fashion). That is, for each training image, the original training dataset can comprise a respective ground-truth annotation that corresponds to that training image. In various aspects, a ground-truth annotation can be any suitable electronic data that indicates a correct or accurate inferencing task result that is known to correspond to a respective training image. Accordingly, the format, size, or dimensionality of a ground-truth annotation can depend upon the inferencing task that the first deep learning neural network is configured to perform (e.g., if the inferencing task is image classification, then each ground-truth annotation can be a correct or accurate classification label corresponding to a respective training image; if the inferencing task is image segmentation, then each ground-truth annotation can be a correct or accurate segmentation mask corresponding to a respective training image; if the inferencing task is image regression, then each ground-truth annotation can be a correct or accurate regression result corresponding to a respective training image).

In various embodiments, there can be a privacy-restricted medical image. In various aspects, the privacy-restricted medical image can be any suitable medical image that depicts any suitable anatomical structures or portions thereof of any suitable medical patient, and that the first deep learning neural network has encountered during deployment. In other words, the first deep learning neural network can be or have been executed on the privacy-restricted medical image. More specifically, the privacy-restricted medical image can be or have been fed to an input layer of the first deep learning neural network, the privacy-restricted medical image can complete or have completed a forward pass through one or more hidden layers of the first deep learning neural network, and an output layer of the first deep learning neural network can compute or have computed an inferencing task result based on activations from the one or more hidden layers of the first deep learning neural network. In various instances, the inferencing task result can be any suitable electronic data whose format, size, or dimensionality can depend upon the inferencing task that the first deep learning neural network is configured to perform (e.g., if the inferencing task is image classification, then the inferencing task result can be a predicted or inferred classification label for the privacy-restricted medical image; if the inferencing task is image segmentation, then the inferencing task result can be a predicted or inferred segmentation mask for the privacy-restricted medical image; if the inferencing task is image regression, then the inferencing task result can be a predicted or inferred regression result for the privacy-restricted medical image). Accordingly, in some cases, the inferencing task result can have diagnostic or prognostic value for whatever medical patient corresponds to the privacy-restricted medical image.

In any case, it can be desired to re-train or fine-tune the first deep learning neural network on the privacy-restricted medical image. In various aspects, any suitable impetus or rationale can trigger such desire for re-training or fine-tuning (e.g., the inferencing task result can be judged by a medical professional to be incorrect or inaccurate; the inferencing task result can indicate values that are rarely outputted by the first deep learning neural network; the privacy-restricted medical image can be judged by a medical professional or by some other machine learning model to have atypical visual properties or otherwise be aberrant). However, the privacy-restricted medical image can, due to applicable laws or regulations, be prohibited from being directly used to re-train or fine-tune the first deep learning neural network (e.g., whatever device is responsible for deploying the first deep learning neural network can itself utilize the privacy-restricted medical image but can be forbidden from sharing the privacy-restricted medical image with whatever device is responsible for re-training the first deep learning neural network). As described herein, the computerized tool can help to facilitate such re-training in compliance with applicable privacy rules or regulations.

In various embodiments, the access component of the computerized tool can electronically access the privacy-restricted medical image or the inferencing task result. For instance, the access component can receive, retrieve, or otherwise obtain the privacy-restricted medical image or the inferencing task result from any suitable centralized or decentralized data structures (e.g., graph data structures, relational data structures, hybrid data structures). Likewise, the access component can electronically access the first deep learning neural network. For instance, the access component can electronically interface or communicate with (e.g., send electronic commands to, read electronic signals from) the first deep learning neural network. In any case, the access component can be considered as a conduit through which other components of the computerized tool can electronically interact with (e.g., read, write, edit, copy, manipulate, execute, activate, deactivate, modify) the privacy-restricted medical image, the inferencing task result, or the first deep learning neural network.

In various embodiments, the synthesis component of the computerized tool can electronically train a second deep learning neural network to synthesize images, using the privacy-restricted medical image as training data. In various aspects, the second deep learning neural network can exhibit any suitable deep learning internal architecture. For example, the second deep learning neural network can include any suitable numbers of any suitable types of layers (e.g., input layer, one or more hidden layers, output layer, any of which can be convolutional layers, dense layers, LSTM layers, transformer layers, non-linearity layers, pooling layers, batch normalization layers, or padding layers). As another example, the second deep learning neural network can include any suitable numbers of neurons in various layers (e.g., different layers can have the same or different numbers of neurons as each other). As yet another example, the second deep learning neural network can include any suitable activation functions (e.g., softmax, sigmoid, hyperbolic tangent, rectified linear unit) in various neurons (e.g., different neurons can have the same or different activation functions as each other). As still another example, the second deep learning neural network can include any suitable interneuron connections or interlayer connections (e.g., forward connections, skip connections, recurrent connections).

Regardless of its internal architecture, the second deep learning neural network can be configured to receive as input a random array having any suitable format, size, or dimensionality (e.g., a two-dimensional matrix whose numerical elements have randomly-assigned values; a three-dimensional tensor whose numerical elements have randomly-assigned values) and to produce as output a synthetic image that visually resembles the privacy-restricted medical image while simultaneously not being identical to the privacy-restricted medical image. As mentioned above, the synthesis component can train the second deep learning neural network using the privacy-restricted medical image as training data. As a non-limiting example, the internal parameters of the second deep learning neural network can be randomly initialized; the second deep learning neural network can be executed on any given random array, thereby causing the second deep learning neural network to synthesize an image; an error between that synthesized image and the privacy-restricted medical image can be computed; the internal parameters of the second deep learning neural network can be updated via backpropagation driven by that error; and such execution-update procedure can be repeated for any suitable number of random arrays. In such cases, the privacy-restricted medical image can be considered as a type of universal ground-truth for the second deep learning neural network. As another non-limiting example, the second deep learning neural network can be a single-image denoising diffusion model (SinDDM). In such case, various down-sampled and noise-injected copies of the privacy-restricted medical image can be treated as the ground-truths for the second deep learning neural network. As yet another non-limiting example, the second deep learning neural network can be a generator from a single-image generative adversarial network (SinGAN). In such case, various down-sampled copies of the privacy-restricted medical image can be treated as the ground-truths for the second deep learning neural network. As even another non-limiting example, the second deep learning neural network can be a decoder of a variational autoencoder. In such case, the privacy-restricted medical image can be considered as a universal ground-truth for the second deep learning neural network.

In any case, the second deep learning neural network can be trained or otherwise configured to receive as input randomized arrays and to synthesize as output fake images that resemble the privacy-restricted medical image. Accordingly, the synthesis component can, post-training, execute the second deep learning neural network on a set of random arrays, thereby yielding a set of synthetic versions of the privacy-restricted medical image. Note that each synthetic version can have the same format, size, or dimensionality as the privacy-restricted medical image (e.g., if the privacy-restricted medical image is a two-dimensional pixel array, then each synthetic version can likewise be a two-dimensional pixel array; if the privacy-restricted medical image is a three-dimensional voxel array, then each synthetic version can likewise be a three-dimensional voxel array). Furthermore, note that each synthetic version can be visually unique, some being more visually similar to the privacy-restricted medical image, and others being less visually similar to the privacy-restricted medical image. Indeed, the visual content or substance of any given synthetic version of the privacy-restricted medical image can depend upon the particular numerical values of whatever random array from which that given synthetic version is generated. Accordingly, subtle, barely-recognizable numerical differences among inputted random arrays can cause non-trivial visual content variation across outputted synthetic versions of the privacy-restricted medical image (e.g., some synthetic versions can lack visual objects or styles that are shown in the privacy-restricted medical image; some synthetic versions can include visual objects or styles that are not shown in the privacy-restricted medical image; some synthetic versions can include distorted or warped versions of visual objects or styles that are shown in the privacy-restricted medical image).

In various embodiments, the filter component of the computerized tool can electronically filter the set of synthetic versions of the privacy-restricted medical image, thereby yielding a set of filtered synthetic versions of the privacy-restricted medical image. In other words, the filter component can remove from the set of synthetic versions whatever fake images that do not satisfy any suitable filtration criteria.

In various aspects, such filtration criteria can include an anatomical structure criterion. As a non-limiting example, the privacy-restricted medical image can be known or deemed to illustrate or depict a target anatomical structure (e.g., a specific body part or organ that is diagnostically or prognostically related to the inferencing task that the first deep learning neural network is configured to perform). In various instances, there can be a third deep learning neural network that is configured to classify, detect, or otherwise recognize the target anatomical structure in inputted medical images. In various cases, the third deep learning neural network can exhibit any suitable deep learning internal architecture. For example, the third deep learning neural network can include any suitable numbers of any suitable types of layers (e.g., input layer, one or more hidden layers, output layer, any of which can be convolutional layers, dense layers, LSTM layers, transformer layers, non-linearity layers, pooling layers, batch normalization layers, or padding layers). As another example, the third deep learning neural network can include any suitable numbers of neurons in various layers (e.g., different layers can have the same or different numbers of neurons as each other). As yet another example, the third deep learning neural network can include any suitable activation functions (e.g., softmax, sigmoid, hyperbolic tangent, rectified linear unit) in various neurons (e.g., different neurons can have the same or different activation functions as each other). As still another example, the third deep learning neural network can include any suitable interneuron connections or interlayer connections (e.g., forward connections, skip connections, recurrent connections).

Regardless of its internal architecture, the third deep learning neural network can be trained (e.g., in supervised, unsupervised, or reinforcement learning fashion) to receive as input any given medical image and to produce as output a classification label indicating whether or not the target anatomical structure is present in the given medical image. Accordingly, the filter component can, in various aspects, execute the third deep learning neural network on each of the set of synthetic versions of the privacy-restricted medical image, thereby yielding a respective classification label for each synthetic version. In various cases, the filter component can remove or filter out from the set of synthetic versions whichever ones are classified by the third deep learning neural network as not depicting the target anatomical structure. Such filtration can help to cause the set of filtered synthetic versions to contain only fake images that would be useful for re-training or fine-tuning of the first deep learning neural network (e.g., since the first deep learning neural network can be configured to perform an inferencing task that is clinically related to the target anatomical structure, synthetic images that lack the target anatomical structure can be unhelpful for re-training the first deep learning neural network).

In various aspects, the filtration criteria can include an embedding criterion. As a non-limiting example, there can be a fourth deep learning neural network that is configured to compress inputted medical images into embeddings (e.g., into dimensionally-reduced latent vector representations). In various instances, the fourth deep learning neural network can exhibit any suitable deep learning internal architecture. For example, the fourth deep learning neural network can include any suitable numbers of any suitable types of layers (e.g., input layer, one or more hidden layers, output layer, any of which can be convolutional layers, dense layers, LSTM layers, transformer layers, non-linearity layers, pooling layers, batch normalization layers, or padding layers). As another example, the fourth deep learning neural network can include any suitable numbers of neurons in various layers (e.g., different layers can have the same or different numbers of neurons as each other). As yet another example, the fourth deep learning neural network can include any suitable activation functions (e.g., softmax, sigmoid, hyperbolic tangent, rectified linear unit) in various neurons (e.g., different neurons can have the same or different activation functions as each other). As still another example, the fourth deep learning neural network can include any suitable interneuron connections or interlayer connections (e.g., forward connections, skip connections, recurrent connections).

Regardless of its internal architecture, the fourth deep learning neural network can be trained (e.g., in an unsupervised encoder-decoder deep learning pipeline) to receive as input any given medical image and to produce as output an embedding that is dimensionally smaller (e.g., in some cases, many orders of magnitude smaller) than the given medical image but that nevertheless represents (albeit in hidden or non-apparent fashion) the visual content of the given medical image. Accordingly, the filter component can, in various aspects, execute the fourth deep learning neural network on the privacy-restricted medical image, thereby yielding a particular embedding for the privacy-restricted medical image. In various instances, the filter component can also execute the fourth deep learning neural network on each of the set of synthetic versions of the privacy-restricted medical image, thereby yielding a respective embedding for each synthetic version. In various cases, the filter component can remove or filter out from the set of synthetic versions whichever ones that have embeddings that are outside of a threshold similarity range with respect to the particular embedding of the privacy-restricted medical image. As a non-limiting example, the filter component can remove from the set of synthetic versions whichever synthetic versions whose embeddings are too different from that of the privacy-restricted medical image. Moreover, as another non-limiting example, the filter component can remove from the set of synthetic versions whichever synthetic versions whose embeddings are too similar to that of the privacy-restricted medical image. Such filtration can help to cause the set of filtered synthetic versions to contain only fake images that are similar enough to the privacy-restricted medical image so as to be useful for re-training of the first deep learning neural network, yet that are simultaneously not so similar as to be subject to whatever privacy laws or regulations apply to the privacy-restricted medical image.

In various aspects, the filtration criteria can include an inferencing task result criterion. As mentioned above, the first deep learning neural network can be or have been executed on the privacy-restricted medical image, thereby yielding a particular inferencing task result. In various instances, the filter component can further execute the first deep learning neural network on each of the set of synthetic versions of the privacy-restricted medical image, thereby yielding a respective inferencing task result for each synthetic version. In various cases, the filter component can remove or filter out from the set of synthetic versions whichever ones that have inferencing task results that are too dissimilar to that of the privacy-restricted medical image. Such filtration can help to cause the set of filtered synthetic versions to contain only fake images that the first deep learning neural network treats similarly to the privacy-restricted medical image (e.g., if the output layer of the first deep learning neural network treats a given synthetic image too differently from how it treats the privacy-restricted medical image, then that given synthetic image can be considered as a poor proxy for the privacy-restricted medical image).

In various aspects, the filtration criteria can include a hidden activation map criterion. As mentioned above, the first deep learning neural network can be or have been executed on the privacy-restricted medical image, thereby yielding a particular inferencing task result. In various instances, a particular hidden layer of the first deep learning neural network can, during such execution, produce or have produced a particular hidden activation map. In various cases, the filter component can execute the first deep learning neural network on each of the set of synthetic versions of the privacy-restricted medical image, thereby yielding a respective hidden activation map produced by that particular hidden layer for each synthetic version. In various aspects, the filter component can remove or filter out from the set of synthetic versions whichever ones that have hidden activation maps that are too dissimilar to that of the privacy-restricted medical image. As above, such filtration can help to cause the set of filtered synthetic versions to contain only fake images that the first deep learning neural network treats similarly to the privacy-restricted medical image (e.g., if hidden layers of the first deep learning neural network treat a given synthetic image too differently from how they treat the privacy-restricted medical image, then that given synthetic image can be considered as a poor proxy for the privacy-restricted medical image).

In various aspects, the filtration criteria can include any suitable image metadata criterion. As a non-limiting example, any suitable image property (e.g., contrast level, brightness level, mean pixel/voxel intensity level, standard deviation of pixel/voxel intensity levels) can be computed for the privacy-restricted medical image, and that image property can likewise be computed for each of the set of synthetic versions. In various instances, the filter component can remove or filter out from the set of synthetic versions whichever ones that have image properties that are outside of a threshold similarity range with respect to that of the privacy-restricted medical image. As a non-limiting example, the filter component can remove from the set of synthetic versions whichever synthetic versions whose image properties are too different from that of the privacy-restricted medical image. Moreover, as another non-limiting example, the filter component can remove from the set of synthetic versions whichever synthetic versions whose image properties are too similar to that of the privacy-restricted medical image. As above, such filtration can help to cause the set of filtered synthetic versions to contain only fake images that are similar enough to the privacy-restricted medical image so as to be useful for re-training of the first deep learning neural network, yet that are simultaneously not so similar as to be subject to whatever privacy laws or regulations apply to the privacy-restricted medical image.

Note that, in some cases, any of the aforementioned filtration criteria can be utilized in whatever error or loss function that is used to train the second deep learning neural network. Indeed, the internal parameters of the second deep learning neural network can (depending upon its particular architecture) be incrementally updated based on a loss function that includes a reconstruction loss term (e.g., error between a synthetic image and the privacy-restricted medical image itself) or an adversarial loss term (e.g., in a GAN, a generator's loss can be equal to or otherwise based on a complement of a discriminator's loss).

Now, in some cases, that loss function can further include an anatomical structure term. That is, for any given synthetic image that is generated by the second deep learning neural network during training, the third deep learning neural network can be executed on that given synthetic image, thereby yielding a classification label indicating whether or not that given synthetic image depicts the target anatomical structure. In various instances, the anatomical structure term can be equal to or otherwise based on an error between that classification label and whatever ground-truth classification label that the third deep learning neural network produces for the privacy-restricted medical image. Thus, the anatomical structure term can be considered as biasing the second deep learning neural network toward synthesis of fake images that depict the target anatomical structure and away from synthesis of fake images that lack the target anatomical structure.

Moreover, in some aspects, the loss function can further include an embedding term. That is, for any given synthetic image that is generated by the second deep learning neural network during training, the fourth deep learning neural network can be executed on that given synthetic image, thereby yielding an embedding for that given synthetic image. In various instances, the embedding term can be equal to or otherwise based on an error between that embedding and whatever ground-truth embedding that the fourth deep learning neural network produces for the privacy-restricted medical image. Note that such error can be defined according to whatever embedding similarity range is utilized by the filter component. Thus, the embedding term can be considered as biasing the second deep learning neural network toward synthesis of fake images whose embeddings are not too different from, but also not too similar to, the ground-truth embedding corresponding to the privacy-restricted medical image.

Furthermore, in some aspects, the loss function can further include an inferencing task result term. That is, for any given synthetic image that is generated by the second deep learning neural network during training, the first deep learning neural network can be executed on that given synthetic image, thereby yielding an inferencing task result for that given synthetic image. In various instances, the inferencing task result term can be equal to or otherwise based on an error between that inferencing task result and whatever inferencing task result that the first deep learning neural network produces or has produced for the privacy-restricted medical image. Thus, the inferencing task result term can be considered as biasing the second deep learning neural network toward synthesis of fake images that are treated by the first deep learning neural network in the same way as the privacy-restricted medical image.

Further still, in some aspects, the loss function can further include a hidden activation map term. That is, for any given synthetic image that is generated by the second deep learning neural network during training, the first deep learning neural network can be executed on that given synthetic image, thereby yielding a hidden activation map for that given synthetic image. In various instances, the hidden activation map term can be equal to or otherwise based on an error between that hidden activation map and whatever hidden activation map that the first deep learning neural network produces or has produced for the privacy-restricted medical image. Thus, the hidden activation map term can be considered as biasing the second deep learning neural network toward synthesis of fake images that are treated by hidden layers of the first deep learning neural network in the same way as the privacy-restricted medical image.

Yet further still, in some aspects, the loss function can further include a metadata term. That is, for any given synthetic image that is generated by the second deep learning neural network during training, any suitable metadata (e.g., pixel/voxel mean, pixel/voxel standard deviation) can be computed for that given synthetic image. In various instances, the metadata term can be equal to or otherwise based on an error between that metadata and whatever ground-truth metadata that is computed for the privacy-restricted medical image. Note that such error can be defined according to whatever metadata similarity range is utilized by the filter component. Thus, the metadata term can be considered as biasing the second deep learning neural network toward synthesis of fake images whose metadata are not too different from, but also not too similar to, the ground-truth metadata corresponding to the privacy-restricted medical image.

In any case, the set of filtered synthetic versions of the privacy-restricted medical image can be considered as being visually similar enough to the privacy-restricted medical image so as to be relevant for re-training of the first deep learning neural network, yet simultaneously being visually distinct enough from the privacy-restricted medical image so as to not be hampered by the privacy laws or regulations that apply to the privacy-restricted medical image.

In various embodiments, the fine-tune component of the computerized tool can electronically transmit or share the set of filtered synthetic versions of the privacy-restricted medical image, but not the privacy-restricted medical image itself, with any suitable computing device that is responsible for re-training or fine-tuning the first deep learning neural network. In various instances, the fine-tune component can instruct or command such computing device to initiate or begin re-training or fine-tuning of the first deep learning neural network using the set of filtered synthetic versions of the privacy-restricted medical image. In this way, the first deep learning neural network can be re-trained or fine-tuned on whatever visual substance is conveyed by the privacy-restricted medical image, without running afoul of privacy laws or regulations that protect the privacy-restricted medical image.

Various embodiments described herein can be employed to use hardware or software to solve problems that are highly technical in nature (e.g., to facilitate medical image privacy preservation via image synthesis and filtration), that are not abstract and that cannot be performed as a set of mental acts by a human. Further, some of the processes performed can be performed by a specialized computer (e.g., medical imaging scanners, deep learning neural networks) for carrying out defined acts related to deep learning. For example, such defined acts can include: accessing, by at least one of one or more devices operatively coupled to a processor, a medical image for which a first artificial neural network has produced an inferencing task result; training, by at least one of the one or more devices, a second artificial neural network on the medical image to perform image synthesis; generating, by at least one of the one or more devices and via execution of the second artificial neural network post-training, a set of synthetic variants of the medical image; and instructing, by at least one of the one or more devices, a computerized device to fine-tune the first artificial neural network using at least some of the set of synthetic variants of the medical image rather than using the medical image.

In various aspects, the medical image can depict a target anatomical structure, and the defined acts can comprise: identifying, by at least one of the one or more devices, within the set of synthetic variants of the medical image, and via execution of another artificial neural network that is trained to classify or detect anatomical structures in inputted images, one or more synthetic variants of the medical image that do not depict the target anatomical structure; and removing, by at least one of the one or more devices, those one or more synthetic variants of the medical image from the set of synthetic variants of the medical image, such that those one or more synthetic variants of the medical image are not used to fine-tune the first artificial neural network.

In various instances, the medical image can correspond to an embedding, and the defined acts can comprise: identifying, by at least one of the one or more devices, within the set of synthetic variants of the medical image, and via execution of another artificial neural network that is trained to create embeddings for inputted images, one or more synthetic variants of the medical image whose embeddings differ by less than a first threshold margin from the embedding of the medical image or by more than a second threshold margin from the embedding of the medical image, wherein the first threshold margin can be less than the second threshold margin; and removing, by at least one of the one or more devices, those one or more synthetic variants of the medical image from the set of synthetic variants of the medical image, such that those one or more synthetic variants of the medical image are not used to fine-tune the first artificial neural network.

In various cases, the defined acts can comprise: generating, by at least one of the one or more devices and via execution of the first artificial neural network, a set of inferencing task results respectively corresponding to the set of synthetic variants of the medical image; identifying, by at least one of the one or more devices and within the set of synthetic variants of the medical image, one or more synthetic variants of the medical image whose inferencing task results differ by more than a threshold margin from the inferencing task result; and removing, by at least one of the one or more devices, those one or more synthetic variants of the medical image from the set of synthetic variants of the medical image, such that those one or more synthetic variants of the medical image are not used to fine-tune the first artificial neural network.

In various aspects, the first artificial neural network can produce a first hidden activation map for the medical image, and the defined acts can comprise: generating, by at least one of the one or more devices and via execution of the first artificial neural network, a set of hidden activation maps respectively corresponding to the set of synthetic variants of the medical image; identifying, by at least one of the one or more devices and within the set of synthetic variants of the medical image, one or more synthetic variants of the medical image whose hidden activation maps differ by more than a threshold margin from the first hidden activation map; and removing, by at least one of the one or more devices, those one or more synthetic variants of the medical image from the set of synthetic variants of the medical image, such that those one or more synthetic variants of the medical image are not used to fine-tune the first artificial neural network.

In various instances, a training loss of the second artificial neural network can be based on any of the aforementioned types of filtration: anatomical structure filtration; embedding filtration; inferencing task result filtration; or hidden activation map filtration.

Such defined acts are not performed manually by humans. Indeed, neither the human mind nor a human with pen and paper can: electronically train an image synthesizer on a privacy-restricted medical image that has been produced by a medical imaging scanner and that has been analyzed by a given model; electronically generate, via the image synthesizer, various synthetic versions of the privacy-restricted medical image by executing the image synthesizer; electronically filter such synthetic versions using anatomical structure classification, embedding computation, inferencing task result computation, or hidden activation map computation (e.g., such filtration can, in some cases, be included in the training loss function of the image synthesizer); and electronically cause the given model to undergo re-training or fine-tuning using the filtered synthetic versions of the privacy-restricted medical image rather than using the privacy-restricted medical image itself. Indeed, medical imaging scanners (e.g., MRI scanners, CT scanners, X-ray scanners) are inherently-computerized, hardware-based constructs that simply cannot be meaningfully implemented in any way by the human mind without computers. Additionally, deep learning neural networks are inherently computerized, software-based constructs that cannot be meaningfully trained or executed in any way by the human mind without computers. In fact, continual learning is itself a computerized monitoring task that is focused on periodically or regularly re-training or fine-tuning deployed neural networks so as to avoid the problem of data drift. It would make no sense whatsoever to discuss the computerized monitoring task of continual learning without regard to computing environments. Accordingly, a computerized tool that can facilitate re-training or fine-tuning of a deployed neural network is likewise inherently-computerized and cannot be implemented in any sensible, practical, or reasonable way without computers.

Moreover, various embodiments described herein can integrate into a practical application various teachings relating to the field of deep learning. As described above, a given neural network can be deployed in the medical field, so as to perform some inferencing task (e.g., image classification, image segmentation, image regression) on medical images depicting anatomical structures of medical patients. To overcome the problem of data drift, the given neural network can be subjected to continual learning: that is, periodic or regular re-training or fine-tuning. Continual learning is effective only when it involves re-training or fine-tuning the given neural network on realistic-looking medical images. However, real medical images of real medical patients are often subject to privacy restrictions that prohibit them from being shared with devices that are equipped to facilitate re-training or fine-tuning. Accordingly, in the real-world, there can be a lack of realistic-looking medical images that are available for continual learning, thereby leaving deployed neural networks vulnerable to data drift.

Various embodiments described herein can address one or more of these technical problems. In particular, when given a privacy-restricted medical image that is desired to be used in continual learning of a particular neural network, various embodiments described herein can involve training a single-image synthesizer on that privacy-restricted medical image. As described herein, the single-image synthesizer can be configured to receive as input random arrays and to produce as output fake images that nevertheless visually resemble the privacy-restricted medical image. In various aspects, various embodiments can involve filtering such fake images, such that they include only fake images that: depict a same target anatomical structure as the privacy-restricted medical image; correspond to a similar-yet-distinct embedded representation as the privacy-restricted medical image; and are treated by (e.g., an output layer or hidden layers of) the particular neural network similarly as the privacy-restricted medical image. In various instances, various embodiments can even leverage such filtration during the training of the single-image synthesizer (e.g., a loss function of the single-image synthesizer can include an anatomical structure term, an embedding term, an inferencing task result term, or a hidden activation map term). In any case, the set of filtered fake image can be considered as being visually, semantically, or otherwise substantively similar enough to the privacy-restricted medical image so as to be useful in re-training of the particular neural network, yet also being visually different enough from the privacy-restricted medical image so as to not be subject to the same privacy laws or regulations as the privacy-restricted medical image. Accordingly, the particular neural network can be re-trained or fine-tuned based on the set of filtered fake images rather than based on the privacy-restricted medical image. Accordingly, various embodiments described herein can be considered as a clever or inventive utilization of single-image synthesizers that facilitates continual learning without violation of applicable privacy restrictions. In other words, various embodiments described herein can be considered as a clever or inventive technique for constructing a re-training dataset for the particular neural network. Thus, various embodiments described herein certainly constitute a tangible and concrete technical improvement or technical advantage in the field of deep learning. Accordingly, such embodiments clearly qualify as useful and practical applications of computers.

Furthermore, various embodiments described herein can control real-world tangible devices based on the disclosed teachings. For example, various embodiments described herein can create synthetic versions of real-world medical images captured by real-world medical imaging scanners (e.g., CT scanner, MRI scanner). Moreover, various embodiments described herein can cause real-world artificial neural networks to be re-trained or fine-tuned based on such synthetic versions of real-world medical images.

It should be appreciated that the herein figures and description provide non-limiting examples of various embodiments and are not necessarily drawn to scale.

FIG. 1 illustrates a block diagram of an example, non-limiting system 100 that can facilitate medical image privacy preservation via image synthesis and filtration in accordance with one or more embodiments described herein. As shown, a privacy system 102 can be electronically integrated, via any suitable wired or wireless electronic connection, with a privacy-restricted medical image 104, with a trained artificial neural network 106, or with an inferencing task result 108.

In various aspects, the trained artificial neural network 106 can exhibit any suitable deep learning internal architecture. Indeed, in various cases, the trained artificial neural network 106 can have an input layer, one or more hidden layers, and an output layer. In various instances, any of such layers can be coupled together by any suitable interneuron connections or interlayer connections, such as forward connections, skip connections, or recurrent connections. Furthermore, in various cases, any of such layers can be any suitable types of neural network layers having any suitable learnable or trainable internal parameters. For example, any of such input layer, one or more hidden layers, or output layer can be convolutional layers, whose learnable or trainable parameters can be convolutional kernels. As another example, any of such input layer, one or more hidden layers, or output layer can be dense layers, whose learnable or trainable parameters can be weight matrices or bias values. As still another example, any of such input layer, one or more hidden layers, or output layer can be batch normalization layers, whose learnable or trainable parameters can be shift factors or scale factors. As even another example, any of such input layer, one or more hidden layers, or output layer can be LSTM layers, whose learnable or trainable parameters can be input-state weight matrices or hidden-state weight matrices. As yet another example, any of such input layer, one or more hidden layers, or output layer can be transformer layers, whose learnable or trainable parameters can be single-head or multi-head attention blocks or other weight matrices. Further still, in various cases, any of such layers can be any suitable types of neural network layers having any suitable fixed or non-trainable internal parameters. For example, any of such input layer, one or more hidden layers, or output layer can be non-linearity layers, padding layers, pooling layers, or concatenation layers.

In various aspects, the trained artificial neural network 106 can be configured to perform any suitable inferencing task on inputted medical images having any suitable format, size, or dimensionality. As a non-limiting example, the trained artificial neural network 106 can be configured to perform the inferencing task on a medical image that is an x-by-y array of pixels, for any suitable positive integers x and y. As another non-limiting example, the trained artificial neural network 106 can be configured to perform the inferencing task on a medical image that is an x-by-y-by-z array of voxels, for any suitable positive integers x, y, and z. Moreover, the trained artificial neural network 106 can be configured to perform the inferencing task on medical images that are captured or generated by any suitable medical imaging modality. As a non-limiting example, the trained artificial neural network 106 can be configured to perform the inferencing task on medical images that are captured or generated by CT scanners, MRI scanners, X-ray scanners, ultrasound scanners, PET scanners, or NM scanners.

In any case, the trained artificial neural network 106 can be configured to receive as input a medical image and to produce as output an inferencing task result for that medical image. In various instances, the format, size, or dimensionality of the inferencing task result can depend upon the inferencing task that the trained artificial neural network 106 is configured to perform. As a non-limiting example, the inferencing task can be image classification. In such case, the inferencing task result can be a classification label that the trained artificial neural network 106 has predicted for the medical image. As another non-limiting example, the inferencing task can be image segmentation. In such case, the inferencing task result can be a segmentation mask that the trained artificial neural network 106 has predicted for the image. As yet another non-limiting example, the inferencing task can be image regression. In such case, the inferencing task result can be a regression output (e.g., denoised image, resolution enhanced image, or other continuously-variable output) that the trained artificial neural network 106 has predicted for the medical image.

In various embodiments, the trained artificial neural network 106 can be previously trained on any suitable training dataset to perform the inferencing task on inputted medical images. In various aspects, that training dataset can comprise any suitable number of training medical images, each of which can be sized or formatted so as to facilitate analysis by the trained artificial neural network 106. As a non-limiting example, suppose that the trained artificial neural network 106 can be configured to operate on x-by-y pixel arrays that are captured or generated by an ultrasound scanner. In such case, each training medical image can be an x-by-y pixel array that has been captured or generated by an ultrasound scanner. As another non-limiting example, suppose that the trained artificial neural network 106 can be configured to operate on x-by-y-by-z voxel arrays that are captured or generated by an NM scanner. In such case, each training medical image can be an x-by-y-by-z voxel array that has been captured or generated by an NM scanner.

In some aspects, that training dataset can be annotated. In such cases, each given training medical image can have a respectively corresponding ground-truth annotation that can indicate or represent a correct or accurate inferencing task result for that given training medical image. In various instances, the ground-truth annotation corresponding to the given training medical image can be any suitable electronic data that indicates, represents, or otherwise conveys a correct or accurate inferencing task result (e.g., correct or accurate classification label, correct or accurate segmentation mask, correct or accurate regression output) that is known or deemed to correspond to the given training medical image.

In situations where that training dataset is annotated, the trained artificial neural network 106 can have previously undergone supervised training with respect to the training dataset (e.g., its trainable internal parameters can be randomly initialized, it can be iteratively executed on the set of training medical images in the training dataset, and its trainable internal parameters can be iteratively updated by backpropagating errors between the outputs it produced during training and the ground-truth annotations in the training dataset). Such training can have involved any suitable error or objective function (e.g., cross-entropy), any suitable optimization algorithm (e.g., stochastic gradient descent), any suitable number of training epochs, or any suitable training batch sizes.

However, this is a mere non-limiting example of how the trained artificial neural network 106 can be trained. In other cases, the training dataset can be unannotated (e.g., the ground-truth annotations can be omitted, unavailable, or unknown). In such cases, the trained artificial neural network 106 can be trained in unsupervised fashion or in reinforcement learning fashion.

In various aspects, the trained artificial neural network 106 can, after having been trained, be deployed in the medical field. That is, the trained artificial neural network 106 can be deployed in a real-world hospital or clinic so as to perform the inferencing task for diagnostic or prognostic purposes associated with real-world medical patients. In various aspects, the privacy-restricted medical image 104 can be any suitable medical image which the trained artificial neural network 106 has encountered during deployment. Thus, the privacy-restricted medical image 104 can depict any suitable anatomical structures or portions thereof of any suitable medical patient, and the trained artificial neural network 106 can be or have been executed on the privacy-restricted medical image 104. In various instances, such execution can yield the inferencing task result 108. More specifically, the privacy-restricted medical image 104 can be or have been fed to an input layer of the trained artificial neural network 106. In various cases, the privacy-restricted medical image 104 can complete or have completed a forward pass through one or more hidden layers of the trained artificial neural network 106. Accordingly, an output layer of the trained artificial neural network 106 can compute or calculate the inferencing task result 108 based on hidden activation maps produced by the one or more hidden layers of the trained artificial neural network 106.

In various aspects, the inferencing task result 108 can be one or more scalars, one or more vectors, one or more matrices, one or more tensors, one or more character strings, or any suitable combination thereof that is, indicates, or otherwise represents a predicted or inferred outcome of performing the inferencing task on the privacy-restricted medical image 104. As a non-limiting example, suppose that the inferencing task is image classification. In such case, the inferencing task result 108 can be a predicted or inferred classification label that the trained artificial neural network 106 has produced for the privacy-restricted medical image 104. As another non-limiting example, suppose that the inferencing task is image segmentation. In such case, the inferencing task result 108 can be a predicted or inferred segmentation mask that the trained artificial neural network 106 has produced for the privacy-restricted medical image 104. As yet another non-limiting example, suppose that the inferencing task is image regression. In such case, the inferencing task result 108 can be a predicted or inferred regression output (e.g., a denoised image, a resolution-enhanced image) that the trained artificial neural network 106 has produced for the privacy-restricted medical image 104.

In various aspects, it can be warranted to subject the trained artificial neural network 106 to re-training or fine-tuning based on the privacy-restricted medical image 104.

As a non-limiting example, a medical professional can conclude or have concluded that the inferencing task result 108 is incorrect or inaccurate for the privacy-restricted medical image 104. Thus, it can be concluded that the privacy-restricted medical image 104 contains some unique or special visual content, pattern, or style that distracted, impeded, or otherwise threw-off the trained artificial neural network 106. Accordingly, re-training or fine-tuning of the trained artificial neural network 106 can be warranted, so as to teach the trained artificial neural network 106 to reliably, confidently, or accurately handle such unique or special visual content, pattern, or style.

As another non-limiting example, it can be the case that the inferencing task result 108, though not necessarily incorrect or inaccurate, represents, occupies, or otherwise comes from a rarely-predicted or infrequently-predicted portion or subset of the possible output space or range of the trained artificial neural network 106. For instance, suppose that the inferencing task is image classification. Moreover, suppose that such image classification includes p distinct classes, a q-th one of which the trained artificial neural network 106 has been found to predict in fewer than any suitable threshold percent of cases (e.g., in fewer than 5% of cases), for any suitable positive integers $q \leq p$. In such case, if the inferencing task result 108 indicates the q-th class, it can be concluded that the privacy-restricted medical image 104 contains some unique or special visual content, pattern, or style that is rarely encountered by the trained artificial neural network 106. Accordingly, re-training or fine-tuning of the trained artificial neural network 106 can be warranted, so as to teach the trained artificial neural network 106 to more reliably, confidently, or accurately handle such unique or special visual content, pattern, or style.

As still another non-limiting example, a medical professional (or even some other machine learning model) can conclude or have concluded that the privacy-restricted medical image 104 is anomalous for any other suitable reason. Thus, it can be concluded that the privacy-restricted medical image 104 contains some unique or special visual content, pattern, or style, and re-training or fine-tuning of the trained artificial neural network 106 can be warranted, so as to teach the trained artificial neural network 106 to reliably, confidently, or accurately handle such unique or special visual content, pattern, or style.

No matter why the trained artificial neural network 106 warrants re-training or fine-tuning on the privacy-restricted medical image 104, the privacy-restricted medical image 104 can (as its name suggests) be subject to one or more privacy laws, regulations, or restrictions that limit sharing or usage of the privacy-restricted medical image 104. Thus, although whatever computerized device that is responsible for deploying the trained artificial neural network 106 might have permission to utilize the privacy-restricted medical image 104, whatever computerized device that is instead responsible for re-training or fine-tuning the trained artificial neural network 106 might not have such permission. Accordingly, the privacy-restricted medical image 104 can be considered as unavailable for re-training or fine-tuning of the trained artificial neural network 106. As described herein, the privacy system 102 can be implemented on whatever computerized device that is responsible for deploying the trained artificial neural network 106 and can nevertheless facilitate such re-training or fine-tuning without violating applicable privacy laws, regulations, or restrictions.

In various embodiments, the privacy system 102 can comprise a processor 110 (e.g., computer processing unit, microprocessor) and a non-transitory computer-readable memory 112 that is operably or operatively or communicatively connected or coupled to the processor 110. The non-transitory computer-readable memory 112 can store computer-executable instructions which, upon execution by the processor 110, can cause the processor 110 or other components of the privacy system 102 (e.g., access component 114, synthesis component 116, filter component 118, fine-tune component 120) to perform one or more acts. In various embodiments, the non-transitory computer-readable memory 112 can store computer-executable components (e.g., access component 114, synthesis component 116, filter component 118, fine-tune component 120), and the processor 110 can execute the computer-executable components.

In various embodiments, the privacy system 102 can comprise an access component 114. In various aspects, the access component 114 can electronically access or otherwise electronically communicate in any suitable fashion with the trained artificial neural network 106. Accordingly, the access component 114 can electronically transmit any suitable electronic data to the trained artificial neural network 106, and the trained artificial neural network 106 can likewise electronically transmit any suitable electronic data to the access component 114. In some instances, the access component 114 can be considered as a proxy or conduit through which other components of the privacy system 102 can interact with, communicate with, or otherwise manipulate the trained artificial neural network 106. In various aspects, the access component 114 can electronically access the privacy-restricted medical image 104 or the inferencing task result 108. That is, the access component 114 can electronically receive, electronically retrieve, or otherwise electronically obtain the privacy-restricted medical image 104 or the inferencing task result 108, from any suitable electronic source, database, or computerized workstation. In any case, the access component 114 can be considered as a proxy or conduit through which other components of the privacy system 102 can interact with, control, or otherwise manipulate the privacy-restricted medical image 104 or the inferencing task result 108. However, these are mere non-limiting examples. In other cases, the access component 114 can be omitted, and any other components of the privacy system 102 can communicate or interact directly with the privacy-restricted medical image 104, the inferencing task result 108, or the trained artificial neural network 106.

In various embodiments, the privacy system 102 can comprise a synthesis component 116. In various aspects, the synthesis component 116 can, as described herein, utilize an image-synthesizer to create multiple synthetic variants of the privacy-restricted medical image 104.

In various embodiments, the privacy system 102 can comprise a filter component 118. In various instances, the filter component 118 can, as described herein, filter or pare down the multiple synthetic variants via any suitable filtration criteria.

In various embodiments, the privacy system 102 can comprise a fine-tune component 120. In various cases, the fine-tune component 120 can, as described herein, instruct any suitable computerized device to re-train or fine-tune the trained artificial neural network 106 using the filtered synthetic variants of the privacy-restricted medical image 104 rather than using the privacy-restricted medical image 104 itself.

Note that, in various instances, the access component 114, the synthesis component 116, the filter component 118, and the fine-tune component 120 can collectively be considered as being one or more software components 113 of the privacy system 102. In various aspects, it should be appreciated that the one or more software components 113 are described primarily herein as comprising four components (e.g., the access component 114, the synthesis component 116, the filter component 118, and the fine-tune component 120) for case of explanation and illustration. However, the one or more software components 113 are not limited to being implemented as exactly such four components in every embodiment. Indeed, in some embodiments, the functionalities described herein of such four components can be combined in any suitable fashions, so as to be implemented in or by fewer than four components (e.g., in some cases, a single component can perform all of the functionalities that are described herein with respect to the access component 114, the synthesis component 116, the filter component 118, and the fine-tune component 120). In other embodiments, the functionalities described herein of such four components can instead be distributed, separated, split, or fragmented in any suitable fashions, so as to be implemented in or by more than four components (e.g., two or more components can facilitate the functionalities that are performable by the access component 114; two or more components can facilitate the functionalities that are performable by the synthesis component 116; two or more components can facilitate the functionalities that are performable by the filter component 118; two or more components can facilitate the functionalities that are performable by the fine-tune component 120).

Figure 2:
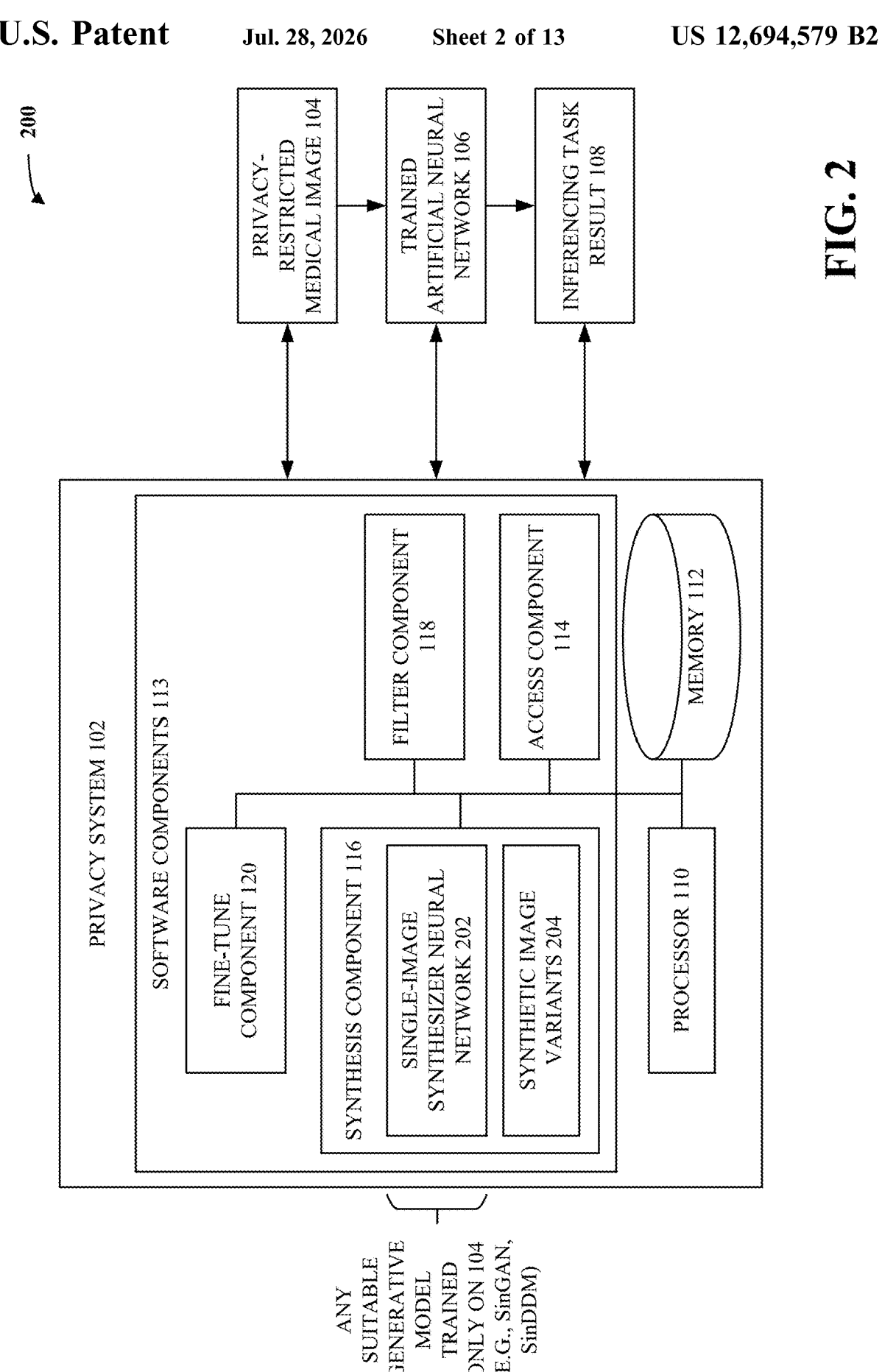
FIG. 2 illustrates a block diagram of an example, non-limiting system including a single-image synthesizer and a set of synthetic image variants that facilitates medical image privacy preservation via image synthesis and filtration in accordance with one or more embodiments described herein.

FIG. 2 illustrates a block diagram of an example, non-limiting system 200 including a single-image synthesizer and a set of synthetic image variants that can facilitate medical image privacy preservation via image synthesis and filtration in accordance with one or more embodiments described herein. As shown, the system 200 can, in some cases, comprise the same components as the system 100, and can further comprise a single-image synthesizer neural network 202 and a plurality of synthetic image variants 204.

In various embodiments, the synthesis component 116 can electronically store, electronically maintain, electronically control, or otherwise electronically access the single-image synthesizer neural network 202. In various aspects, the single-image synthesizer neural network 202 can exhibit any suitable deep learning internal architecture. Indeed, in various cases, the single-image synthesizer neural network 202 can have an input layer, one or more hidden layers, and an output layer. In various instances, any of such layers can be coupled together by any suitable interneuron connections or interlayer connections, such as forward connections, skip connections, or recurrent connections. Furthermore, in various cases, any of such layers can be any suitable types of neural network layers having any suitable learnable or trainable internal parameters. For example, any of such input layer, one or more hidden layers, or output layer can be convolutional layers, whose learnable or trainable parameters can be convolutional kernels. As another example, any of such input layer, one or more hidden layers, or output layer can be dense layers, whose learnable or trainable parameters can be weight matrices or bias values. As still another example, any of such input layer, one or more hidden layers, or output layer can be batch normalization layers, whose learnable or trainable parameters can be shift factors or scale factors. As even another example, any of such input layer, one or more hidden layers, or output layer can be LSTM layers, whose learnable or trainable parameters can be input-state weight matrices or hidden-state weight matrices. As yet another example, any of such input layer, one or more hidden layers, or output layer can be transformer layers, whose learnable or trainable parameters can be single-head or multi-head attention blocks or other weight matrices. Further still, in various cases, any of such layers can be any suitable types of neural network layers having any suitable fixed or non-trainable internal parameters. For example, any of such input layer, one or more hidden layers, or output layer can be non-linearity layers, padding layers, pooling layers, or concatenation layers.

Regardless of its particular internal architecture (e.g., regardless of its specific types or arrangement of layers), the single-image synthesizer neural network 202 can (as its name suggests) be trained only on the privacy-restricted medical image 104 to synthesize images. More specifically, the single-image synthesizer neural network 202 can be configured to receive as input a randomized array and to produce as output a fake image that is based on that randomized array and that visually resembles the privacy-restricted medical image 104. In various aspects, the randomized array can have a format, size, or dimensionality that is less than or equal to that of the privacy-restricted medical image 104. For instance, if the privacy-restricted medical image 104 is an x-by-y array of pixels, then the randomized array can be an a-by-b array of random scalars, for any suitable positive integers $a \leq x$ and $b \leq y$. As another instance, if the privacy-restricted medical image 104 is an x-by-y-by-z array of voxels, then the randomized array can be an a-by-b-by-c array of random scalars, for any suitable positive integers $a \leq x$, $b \leq y$, and $c \leq z$.

In any case, the synthesis component 116 can electronically train the single-image synthesizer neural network 202 to convert randomized arrays into fake images that visually resemble the privacy-restricted medical image 104.

As a non-limiting example, such training can proceed as follows. In various aspects, prior to beginning training, the synthesis component 116 can electronically initialize in any suitable fashion (e.g., random initialization) the trainable internal parameters (e.g., convolutional kernels, weight matrices, bias values) of the single-image synthesizer neural network 202. In various instances, the synthesis component 116 can execute the single-image synthesizer neural network 202 on any suitable randomized array, and such execution can cause the single-image synthesizer neural network 202 to produce some output. More specifically, the synthesis component 116 can feed or route the randomized array to the input layer of the single-image synthesizer neural network 202. In various cases, the randomized array can complete a forward pass through the one or more hidden layers of the single-image synthesizer neural network 202. In various aspects, the output layer of the single-image synthesizer neural network 202 can compute the output based on activation maps or feature maps provided by the one or more hidden layers of the single-image synthesizer neural network 202. Note that the format, size, or dimensionality of the output can be dictated by the number, arrangement, sizes, or other characteristics of the neurons, convolutional kernels, attention blocks, or other internal parameters of the output layer (or of any other layers) of the single-image synthesizer neural network 202. Accordingly, the output can be forced to have any desired format, size, or dimensionality, by adding, removing, or otherwise adjusting characteristics of the output layer (or of any other layers) of the single-image synthesizer neural network 202. So, in various instances, the output can be forced to have a same format, size, or dimensionality as the privacy-restricted medical image 104, and the output can thus be considered as being a predicted or inferred approximation of the privacy-restricted medical image 104. In other words, the privacy-restricted medical image 104 can be considered as a ground-truth that corresponds to the randomized array. Note that, if the single-image synthesizer neural network 202 has so far undergone no or little training, then the output can be highly inaccurate (e.g., can be look nothing like the privacy-restricted medical image 104). In various aspects, the synthesis component 116 can electronically compute any suitable error or loss (e.g., mean absolute error (MAE), mean squared error (MSE), cross-entropy error) between the output and the privacy-restricted medical image 104. Note that this can be considered as a reconstruction error or loss. In various instances, the synthesis component 116 can incrementally update the trainable internal parameters of the single-image synthesizer neural network 202 via backpropagation (e.g., stochastic gradient descent) based on the computed error or loss. In various cases, such execution-and-update procedure can be repeated for any suitable number randomized arrays. This can ultimately cause the trainable internal parameters of the single-image synthesizer neural network 202 to become iteratively optimized for accurately converting randomized arrays into fake images that visually resemble the privacy-restricted medical image 104. In various aspects, the synthesis component 116 can implement any suitable training batch sizes, any suitable error or loss functions, or any suitable training termination criteria during such training.

As another non-limiting example, the synthesis component 116 can electronically train the single-image synthesizer neural network 202 using a SinGAN technique or pipeline. In such case, there can be a pyramid of generators $\{G_H, \ldots, G_0\}$ and a respectively corresponding pyramid of discriminators $\{D_H, \ldots, D_0\}$ trained against an image pyramid of $\{I_H, \ldots, I_0\}$, where $I_h$ can be the privacy-restricted medical image 104 downsampled by a factor of $r^h$ for any suitable integers $0 \leq h \leq H$ and $r > 1$. So, $I_0$ can be the privacy-restricted medical image 104 itself. Each generator $G_h$ can be trained in adversarial fashion with a respective discriminator $D_h$. More specifically, let $Z_h$ be any randomized array having the same format, size, or dimensionality as $I_h$. In various cases, the generator $G_H$ can be configured to receive as input $Z_H$ and to produce as output $\tilde{I}_H$, which can be considered as a predicted or inferred reconstruction of $I_H$. In contrast, every remaining generator $G_{h*}$ for any suitable integer $0 \leq h* < H$ can be configured to receive as input both $Z_{h*}$ and an upsampled version of $\tilde{I}_{h*+1}$ and to produce as output $\tilde{I}_h'$. Each discriminator $D_h$ can be configured to determine whether an inputted image at scale h is genuine (e.g., $I_h$ is known to be genuine) or fake (e.g., $\tilde{I}_h$ is known to be fake). Accordingly, the pyramid of generators $\{G_H, \ldots, G_0\}$ can be executed in coarse to fine fashion (e.g., starting at h=H and ending at h=0), and each generator $G_h$ can be trained using both an adversarial loss (e.g., complement of whatever MAE, MSE, or cross-entropy error is computed for the discriminator $D_h$) and a reconstruction loss (e.g., MAE, MSE, or cross-entropy between $I_h$ and $\tilde{I}_h$). Such training can be repeated for any suitable number iterations or epochs, thereby causing the collective internal parameters of the pyramid of generators $\{G_H, \ldots, G_0\}$ to become iteratively optimized for converting any randomized array at scale H into a full-sized fake image that visually resembles the privacy-restricted medical image 104. Thus, in such cases, the single-image synthesizer neural network 202 can be considered as being or comprising the pyramid of generators $\{G_H, \ldots, G_0\}$.

As still another non-limiting example, the synthesis component 116 can electronically train the single-image synthesizer neural network 202 using a SinDDM technique or pipeline. In such case, there can be an image pyramid qjof $\{I_H, \ldots, I_0\}$, where $I_h$ can be the privacy-restricted medical image 104 downsampled by a factor of $r^h$ for any suitable integers $0 \leq h \leq H$ and $r > 1$. Again, $I_0$ can thus be the privacy-restricted medical image 104 itself. Additionally, there can be a pyramid of blurry images $\{B_H, \ldots, B_0\}$, where $B_H = I_H$, and where $B_{h*}$ is $I_{h*+1}$ upsampeld by r, for any suitable integer $0 \leq h* < H$. Each scale h can include a total of T time steps, for any suitable positive integer T, and each time step t for $0 \leq t \leq T$ can involve the creation of a noise-diffused image $$D_h^t$$

that is any suitable function of: t; h; $B_h$; and $I_h$. For instance, such function can involve weighting $B_h$ and $I_h$ with variable coefficients (or complements thereof) that monotonically increase or decrease with t and summing such weighted quantities. In various aspects, let $Z_h$ be any randomized array having the same format, size, or dimensionality as $I_h$. In various instances, there can be a fully-convolutional denoising model that is configured to receive as input: an image; a scale; and a time-step. More specifically, at scale H and time-step 0, the fully-convolutional denoising model can receive as input $Z_H$, the scale integer H, and the time-step integer 0 and can produce output $$\tilde{I}_H^0,$$

which can be considered as an incrementally-denoised version of $Z_H$ that is predicted or inferred by the fully-convolutional denoising model. Then, for all remaining time-steps at scale H, the fully-convolutional denoising model can receive as input $$\hat{I}_H^{t-1},$$

the scale integer H, and the time-step integer t and can produce as output $$\hat{I}_H^{t},$$

which can be considered as an incrementally-denoised version of $$\hat{I}_H^{t-1}.$$

Note that $$\hat{I}_H^{T}$$

can be considered as being whatever clean or completely-denoised image that the fully-convolutional denoising model has predicted or inferred at scale H. Now, for time-step 0 at all remaining scales h*, the fully-convolutional denoising model can receive as input $Z_{h*}$ combined with $$\hat{I}_{h^*+1}^{T}$$

upsampled by r, the scale integer h*, and the time-step integer 0 and can produce as output $$\hat{I}_{h^*}^{0},$$

which can be considered as the incrementally-denoised version of the combination of $Z_{h*}$ and the upsampled version of $$\hat{I}_{h^*+1}^{T}$$

that is predicted or inferred by the fully-convolutional denoising model. Iterative execution of the fully-convolutional denoising model in order of increasing time-steps and decreasing scales can ultimately yield $$\hat{I}_{0}^{T},$$

which can be considered as a full-sized, completely denoised image predicted or inferred by the fully-convolutional denoising model. In various aspects, the fully-convolutional denoising model can be trained using a reconstruction loss at each scale-and-time-step tuple (h,t) (e.g., MAE, MSE, or cross $$\hat{I}_h^{t} \text{ and } D_h^{t}).$$

Such training can be repeated for any suitable number of iterations or epochs, thereby causing the internal parameters of the fully-convolutional denoising model to become iteratively optimized for converting any randomized array at scale H into a full-sized fake image that visually resembles the privacy-restricted medical image 104. Thus, in such cases, the single-image synthesizer neural network 202 can be considered as being or comprising the fully-convolutional denoising model.

As still another non-limiting example, the synthesis component 116 can electronically train the single-image synthesizer neural network 202 using a variational autoencoder technique or pipeline. In such case, there can be an encoder model and a decoder model. In various aspects, the encoder model can be configured to receive as input an image to produce as output an embedding that represents that inputted image in a compressed or latent fashion (e.g., the embedding can have orders of magnitude fewer numerical elements than the inputted image; yet, the embedding can nevertheless represent, albeit in hidden fashion, at least some substantive visual information of the inputted image), and the decoder model can be configured to receive as input that embedding and to produce as output a reconstructed version of the inputted image. Note that the encoder model and decoder model can be considered as forming a bottle-neck architecture with each other. So, the synthesis component can electronically initialize in any suitable fashion (e.g., random initialization) the trainable internal parameters (e.g., convolutional kernels, weight matrices, bias values) of the encoder model and the decoder model. In various instances, the synthesis component 116 can execute the encoder model on the privacy-restricted medical image 104, and such execution can cause the encoder model to produce some first output. More specifically, the synthesis component 116 can feed or route the privacy-restricted medical image 104 to an input layer of the encoder model, the privacy-restricted medical image 104 can complete a forward pass through one or more hidden layers of the encoder model, and an output layer of the encoder model can compute the first output based on activation maps or feature maps provided by the one or more hidden layers of the encoder model. Note that the format, size, or dimensionality of the first output can be dictated by the number, arrangement, sizes, or other characteristics of the neurons, convolutional kernels, attention blocks, or other internal parameters of the output layer (or of any other layers) of the encoder model. Accordingly, the first output can be forced to have a smaller format, size, or dimensionality than the privacy-restricted medical image 104, by adding, removing, or otherwise adjusting characteristics of the output layer (or of any other layers) of the encoder model. So, in various instances, the first output can be considered as being a predicted or inferred embedding of the privacy-restricted medical image 104. Note that, if the encoder model has so far undergone no or little training, then the first output can be highly inaccurate (e.g., can be not a proper embedding of the privacy-restricted medical image 104).

Now, in various aspects, the synthesis component 116 can execute the decoder model on the first output, and such execution can cause the decoder model to produce some second output. More specifically, the synthesis component 116 can feed or route the first output to an input layer of the decoder model, the first output can complete a forward pass through one or more hidden layers of the decoder model, and an output layer of the decoder model can compute the second output based on activation maps or feature maps provided by the one or more hidden layers of the decoder model. Note that the format, size, or dimensionality of the second output can be dictated by the number, arrangement, sizes, or other characteristics of the neurons, convolutional kernels, attention blocks, or other internal parameters of the output layer (or of any other layers) of the decoder model. Accordingly, the second output can be forced to have the same format, size, or dimensionality as the privacy-restricted medical image 104, by adding, removing, or otherwise adjusting characteristics of the output layer (or of any other layers) of the decoder model. So, in various instances, the second output can be considered as being a predicted or inferred reconstruction of the privacy-restricted medical image 104. Note that, if the decoder model has so far undergone no or little training, then the second output can be highly inaccurate (e.g., can be not a proper reconstruction of the privacy-restricted medical image 104). In various aspects, the synthesis component 116 can electronically compute any suitable error or loss (e.g., MAE, MSE, cross-entropy error) between the second output and the privacy-restricted medical image 104 (again, this can be considered as a reconstruction error or loss). In various instances, the synthesis component 116 can incrementally update the trainable internal parameters of the encoder model and the decoder model via backpropagation (e.g., stochastic gradient descent) based on the computed error or loss.

In various cases, such execution-and-update procedure can be repeated for any suitable number of iterations, epochs, or batches. This can ultimately cause the trainable internal parameters of the encoder model to become iteratively optimized for accurately generating embeddings of inputted images, and can also ultimately cause the trainable internal parameters of the decoder model to become iteratively optimized for accurately reconstructing images from inputted embeddings. Note that, after such training, the decoder model can be executed on any suitable randomized arrays that have the same format, size, or dimensionality as the embeddings produced by the encoder model, and such executions can cause the decoder model to reconstruct whatever images it predicts or infers correspond to those randomized arrays. Because only the privacy-restricted medical image 104 can be used in the aforementioned training, all images reconstructed by the decoder model can visually resemble the privacy-restricted medical image 104. Thus, in various instances, the single-image synthesizer neural network 202 can be or comprise the decoder model.

Although the herein disclosure has so far mainly described the single-image synthesizer neural network 202 as being trained only on the privacy-restricted medical image 104, these are mere non-limiting examples for ease of explanation and illustration. In various embodiments, the single-image synthesizer neural network 202 can be any suitable image synthesizer that is or was pre-trained on any suitable other images that belong to the same medical imaging modality as the privacy-restricted medical image 104, and the privacy-restricted medical image 104 (or any suitable upsampled, downsampled, or noise-injected versions or portions thereof) can be treated as a ground-truth to fine-tune that pre-trained image synthesizer.

In any case, the single-image synthesizer neural network 202 can be any suitable generative artificial neural network that can be trained on the privacy-restricted medical image 104 so as to convert any given randomized array into a fake image that visually resembles the privacy-restricted medical image 104. Accordingly, the synthesis component 116 can leverage the single-image synthesizer neural network 202 to generate the plurality of synthetic image variants 204. Non-limiting aspects are described with respect to FIGS. 3-4.

Figure 3:
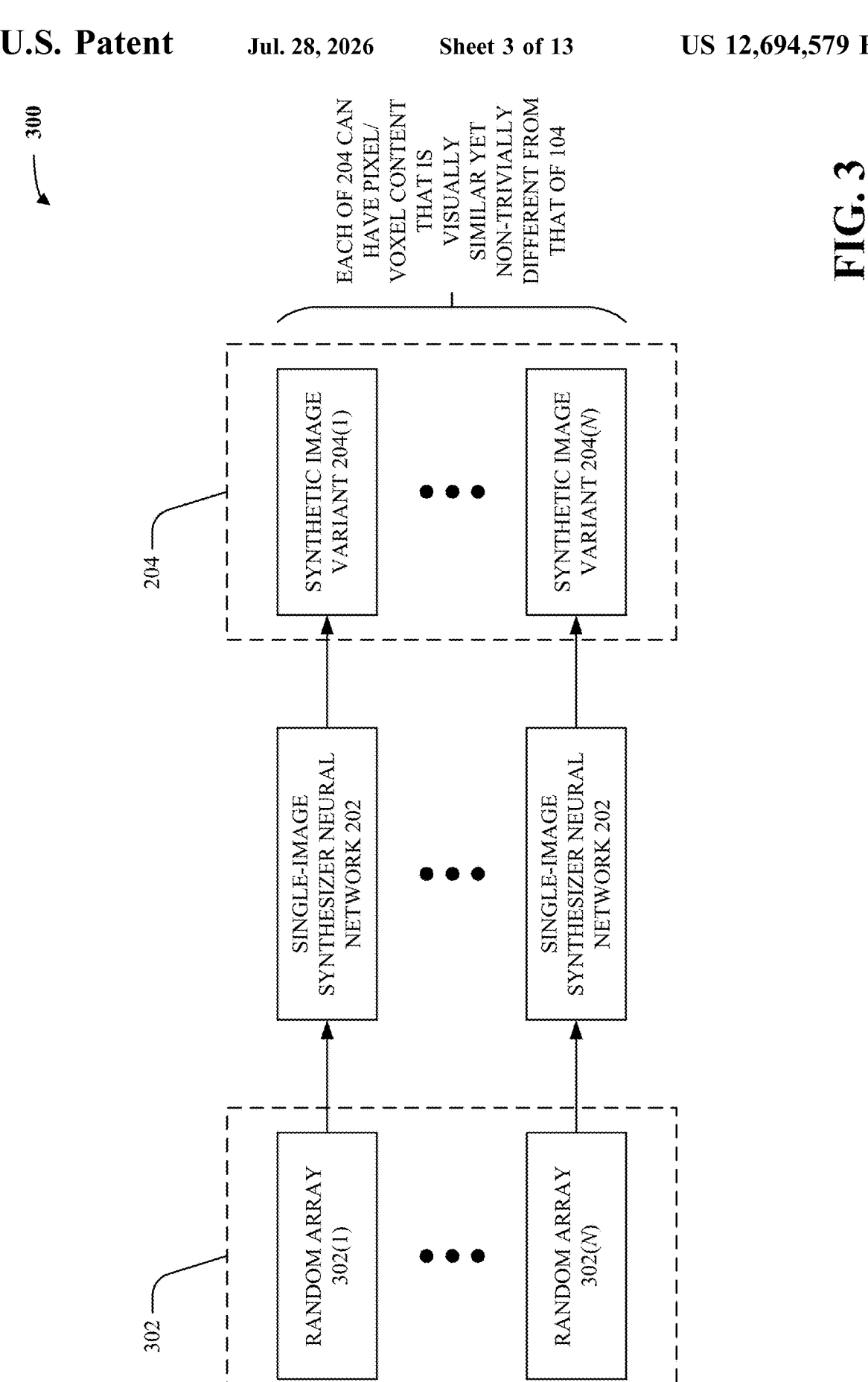
FIG. 3 illustrates an example, non-limiting block diagram showing how a single-image synthesizer can generate a set of synthetic image variants in accordance with one or more embodiments described herein.

FIG. 3 illustrates an example, non-limiting block diagram 300 showing how the single-image synthesizer neural network 202 can generate the plurality of synthetic image variants 204 in accordance with one or more embodiments described herein.

In various embodiments, there can be a plurality of random arrays 302. In various aspects, the plurality of random arrays 302 can comprise n arrays, for any suitable positive integer n: a random array 302(1) to a random array 302($n$). In various instances, each of the plurality of random arrays 302 can have whatever format, size, or dimensionality that the single-image synthesizer neural network 202 is configured to receive as input. In various cases, the synthesis component 116 can execute the single-image synthesizer neural network 202 on each of the plurality of random arrays 302, thereby yielding the plurality of synthetic image variants 204.

As a non-limiting example, the synthesis component 116 can execute the single-image synthesizer neural network 202 on the random array 302(1), thereby yielding a synthetic image variant 204(1). For instance, the random array 302(1) can be fed or routed to the input layer of the single-image synthesizer neural network 202, the random array 302(1) can complete a forward pass through the one or more hidden layers of the single-image synthesizer neural network 202, and the output layer of the single-image synthesizer neural network 202 can compute or calculate the synthetic image variant 204(1) based on hidden activation maps produced by the one or more hidden layers of the single-image synthesizer neural network 202. However, this is a mere non-limiting example of how the single-image synthesizer neural network 202 can be executed on the random array 302(1). It is to be understood and appreciated that pyramidal execution can be implemented in situations where the single-image synthesizer neural network 202 is trained via a SinGAN technique or SinDDM technique. In any case, the synthetic image variant 204(1) can have the same format, size, or dimensionality as the privacy-restricted medical image 104 (e.g., if the privacy-restricted medical image 104 is an x-by-y pixel array, then the synthetic image variant 204(1) can likewise be an x-by-y pixel array; if the privacy-restricted medical image 104 is an x-by-y-by-z voxel array, then the synthetic image variant 204(1) can likewise be an x-by-y-by-z voxel array) and can visually or stylistically resemble the privacy-restricted medical image 104. However, the synthetic image variant 204(1) can be not identical to the privacy-restricted medical image 104. Indeed, the synthetic image variant 204(1) can have non-trivially different visual content than the privacy-restricted medical image 104. After all, the precise visual content of the synthetic image variant 204(1) can be based on the specific numerical values of the random array 302(1). So, in some instances, the particular numerical values of the random array 302(1) can cause the synthetic image variant 204(1) to lack a visual object (e.g., body part, organ, pathology, artifact) that is present in the privacy-restricted medical image 104. In other instances, the particular numerical values of the random array 302(1) can cause the synthetic image variant 204(1) to include a visual object that is absent from the privacy-restricted medical image 104. In yet other instances, the particular numerical values of the random array 302(1) can cause the synthetic image variant 204(1) to include a distorted, warped, resized, reoriented, or reposi-tioned version of a visual object that is present in the privacy-restricted medical image 104.

As another non-limiting example, the synthesis compo-nent 116 can execute the single-image synthesizer neural network 202 on the random array 302(n), thereby yielding a synthetic image variant 204(n). For instance, the random array 302(n) can be fed or routed to the input layer of the single-image synthesizer neural network 202, the random array 302(n) can complete a forward pass through the one or more hidden layers of the single-image synthesizer neural network 202, and the output layer of the single-image synthesizer neural network 202 can compute or calculate the synthetic image variant 204(n) based on hidden activation maps produced by the one or more hidden layers of the single-image synthesizer neural network 202. As above, it is to be understood and appreciated that pyramidal execution can be implemented in situations where the single-image synthesizer neural network 202 is trained via a SinGAN technique or SinDDM technique. In any case, the synthetic image variant 204(n) can have the same format, size, or dimensionality as the privacy-restricted medical image 104 and can visually or stylistically resemble the privacy-re-stricted medical image 104. But, also as above, the synthetic image variant 204(n) can be not identical to the privacy-restricted medical image 104. Indeed, the synthetic image variant 204(n) can have non-trivially different visual content than the privacy-restricted medical image 104. After all, the precise visual content of the synthetic image variant 204(n) can be based on the specific numerical values of the random array 302(n). So, in some instances, the particular numerical values of the random array 302(n) can cause the synthetic image variant 204(n) to lack a visual object that is present in the privacy-restricted medical image 104. In other instances, the particular numerical values of the random array 302(n) can cause the synthetic image variant 204(n) to include a visual object that is absent from the privacy-restricted medi-cal image 104. In yet other instances, the particular numeri-cal values of the random array 302(n) can cause the synthetic image variant 204(n) to include a distorted, warped, resized, reoriented, or repositioned version of a visual object that is present in the privacy-restricted medical image 104.

In various cases, the synthetic image variant 204(1) to the synthetic image variant 204(n) can collectively be consid-ered as the plurality of synthetic image variants 204. Note that, since the specific numerical values of each of the plurality of random arrays 302 can be unique or different from each other, the visual contents of each of the plurality of synthetic image variants 204 can be unique or different from each other. In other words, each of the plurality of synthetic image variants 204 can be considered as a unique, distinct version or variation of the privacy-restricted medical image 104. Accordingly, some of the plurality of synthetic image variants 204 can be considered as being more visually similar to the privacy-restricted medical image 104, whereas others of the plurality of synthetic image variants 204 can be considered as being less visually similar to the privacy-restricted medical image 104. Nevertheless, all of the plu-rality of synthetic image variants 204 can bear a recogniz-able visual relationship to the privacy-restricted medical image 104.

Figure 4:
FIG. 4 illustrates an example, non-limiting block diagram showing some real-world examples of synthetic image variants in accordance with one or more embodiments described herein.

FIG. 4 illustrates an example, non-limiting block diagram 400 showing some real-world examples of synthetic image variants in accordance with one or more embodiments described herein.

As shown, FIG. 4 includes an ultrasound scanned image that can be considered as a non-limiting example of the privacy-restricted medical image 104. In the non-limiting example of FIG. 4, the privacy-restricted medical image 104 depicts an abdominal cavity of a medical patient. Now, a non-limiting embodiment of the single-image synthesizer neural network 202 was reduced to practice and was used to create synthetic variants of the privacy-restricted medical image 104. Such reduction to practice created a first syn-thetic image variant 402, a second synthetic image variant 404, a third synthetic image variant 406, and a fourth synthetic image variant 408. As shown, the first synthetic image variant 402 has only subtle content differences with the privacy-restricted medical image 104. In other words, the first synthetic image variant 402 is quite visually similar to the privacy-restricted medical image 104. As also shown, the second synthetic image variant 404 has more noticeable content differences with the privacy-restricted medical image 104. Indeed, the second synthetic image variant 404 lacks some small objects that are present in the privacy-restricted medical image 104, and the second synthetic image variant 404 has repositioned versions of some large objects that are present in the privacy-restricted medical image 104. Nevertheless, the second synthetic image variant 404 bears a visual resemblance to the privacy-restricted medical image 104. As also shown, the third synthetic image variant 406 has even more noticeable content differences with the privacy-restricted medical image 104. Indeed, the third synthetic image variant 406 conspicuously lacks an inferior vena cava, which is present in the privacy-restricted medical image 104. But again, the third synthetic image variant 406 nevertheless bears a visual resemblance to the privacy-restricted medical image 104. Lastly, as shown, the fourth synthetic image variant 408 has significantly notice-able content differences with the privacy-restricted medical image 104. Indeed, the fourth synthetic image variant 408 lacks many large objects that are present in the privacy-restricted medical image 104. Notwithstanding such signifi-cant content differences, there is nonetheless a visual rela-tionship between the fourth synthetic image variant 408 and the privacy-restricted medical image 104.

As these non-limiting examples show, each of the plural-ity of synthetic image variants 204 can be both: visually reminiscent of the privacy-restricted medical image 104; and visually distinct from the privacy-restricted medical image 104.

Figure 5:
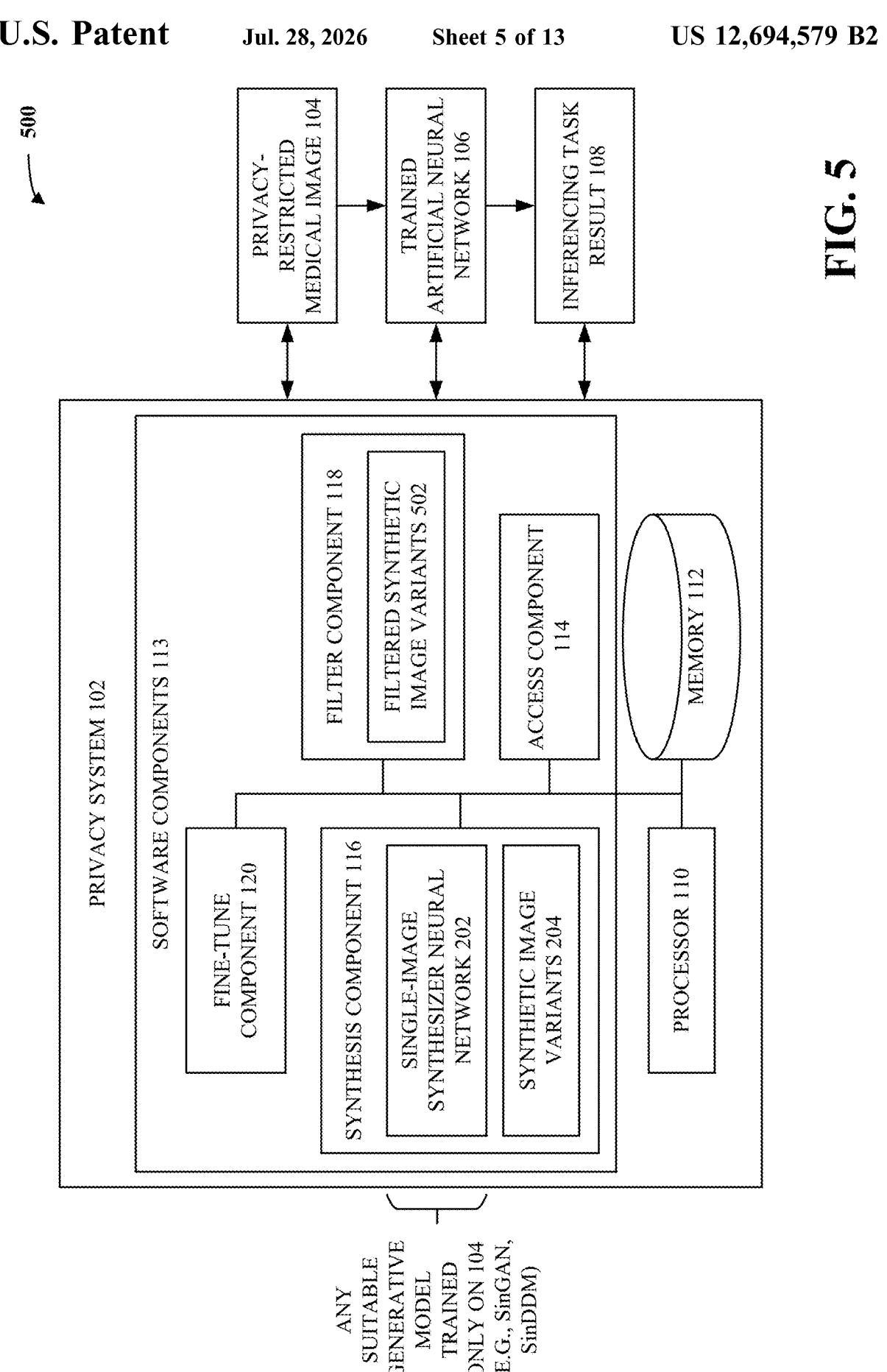
FIG. 5 illustrates a block diagram of an example, non-limiting system including a set of filtered synthetic image variants that facilitates medical image privacy preservation via image synthesis and filtration in accordance with one or more embodiments described herein.

FIG. 5 illustrates a block diagram of an example, non-limiting system 500 including a set of filtered synthetic image variants that can facilitate medical image privacy preservation via image synthesis and filtration in accordance with one or more embodiments described herein. As shown, the system 500 can, in some cases, comprise the same components as the system 200, and can further comprise a plurality of filtered synthetic image variants 502.

In various embodiments, the filter component 118 can electronically apply any suitable filtration criteria to the plurality of synthetic image variants 204, thereby yielding the plurality of filtered synthetic image variants 502. Thus, the plurality of filtered synthetic image variants 502 can be any suitable strict subset of the plurality of synthetic image variants 204 that satisfy or comply with such filtration criteria. Non-limiting aspects are described with respect to FIGS. 6-9.

FIGS. 6-9 illustrate example, non-limiting block diagrams 600, 700, 800, and 900 showing how the plurality of synthetic image variants 204 can be filtered in accordance with one or more embodiments described herein.

Figure 6:
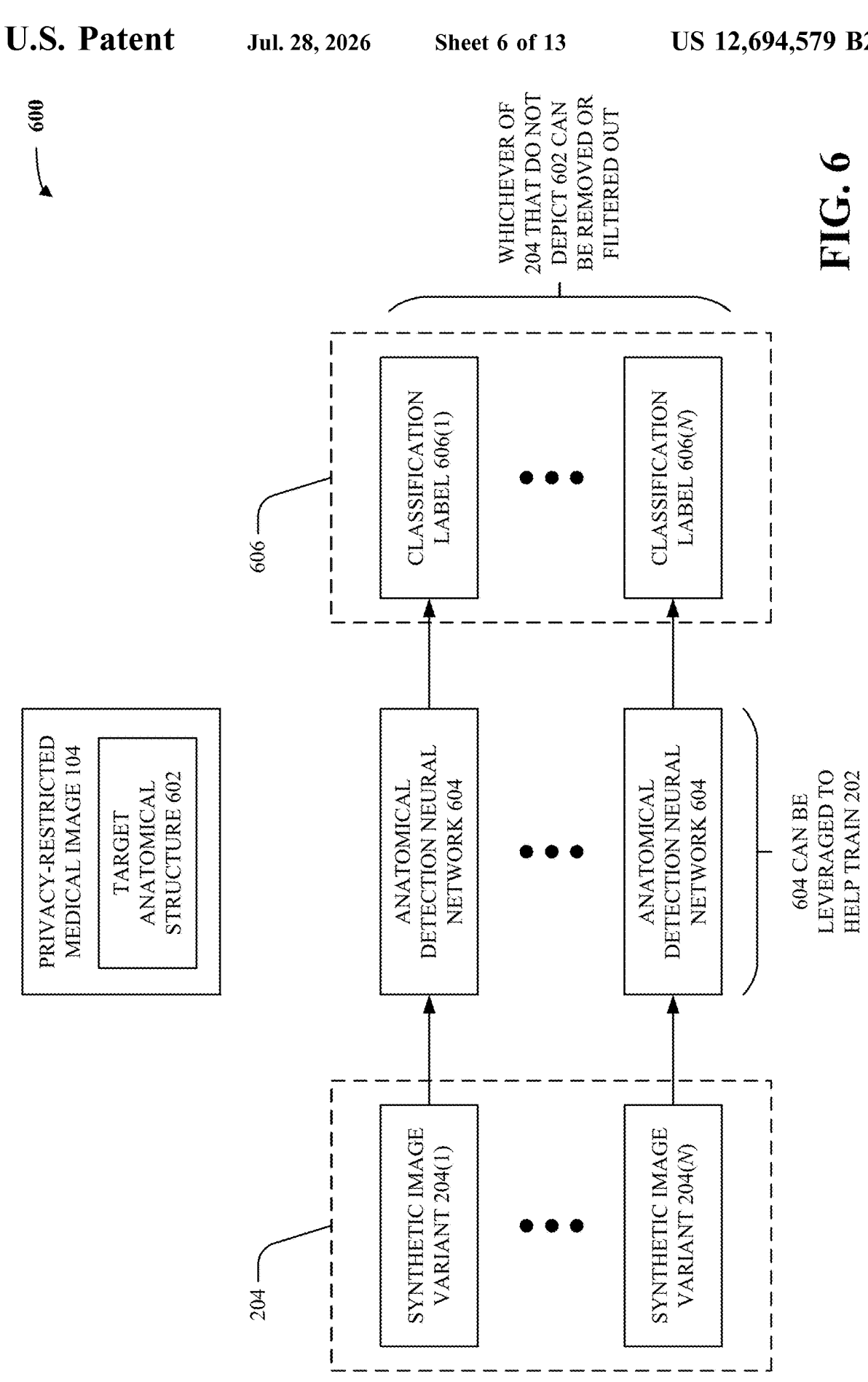
FIGS. 6-9 illustrate example, non-limiting block diagrams showing how synthetic image variants can be filtered in accordance with one or more embodiments described herein.

First, consider FIG. 6. In various embodiments, the filter component 118 can electronically apply anatomical structure filtration to the plurality of synthetic image variants 204.

More specifically, the privacy-restricted medical image 104 can visually depict or show a target anatomical structure 602, where the target anatomical structure 602 can be any suitable body part, tissue, organ, implant, pathology, or portion thereof that is clinically relevant to whatever inferencing task that the trained artificial neural network 106 is configured to perform (e.g., the trained artificial neural network 106 can produce inferencing task results that are diagnostically or prognostically related to the target anatomical structure 602).

In various aspects, the filter component 118 can electronically store, electronically maintain, electronically control, or otherwise electronically access an anatomical detection neural network 604. In various aspects, the anatomical detection neural network 604 can exhibit any suitable deep learning internal architecture. Indeed, in various cases, the anatomical detection neural network 604 can have an input layer, one or more hidden layers, and an output layer. In various instances, any of such layers can be coupled together by any suitable interneuron connections or interlayer connections, such as forward connections, skip connections, or recurrent connections. Furthermore, in various cases, any of such layers can be any suitable types of neural network layers having any suitable learnable or trainable internal parameters. For example, any of such input layer, one or more hidden layers, or output layer can be convolutional layers, whose learnable or trainable parameters can be convolutional kernels. As another example, any of such input layer, one or more hidden layers, or output layer can be dense layers, whose learnable or trainable parameters can be weight matrices or bias values. As still another example, any of such input layer, one or more hidden layers, or output layer can be batch normalization layers, whose learnable or trainable parameters can be shift factors or scale factors. As even another example, any of such input layer, one or more hidden layers, or output layer can be LSTM layers, whose learnable or trainable parameters can be input-state weight matrices or hidden-state weight matrices. As yet another example, any of such input layer, one or more hidden layers, or output layer can be transformer layers, whose learnable or trainable parameters can be single-head or multi-head attention blocks or other weight matrices. Further still, in various cases, any of such layers can be any suitable types of neural network layers having any suitable fixed or non-trainable internal parameters. For example, any of such input layer, one or more hidden layers, or output layer can be non-linearity layers, padding layers, pooling layers, or concatenation layers.

Regardless of its particular internal architecture, the anatomical detection neural network 604 can (as its name suggests) be trained (e.g., in supervised, unsupervised, or reinforcement learning fashion) to detect the target anatomical structure 602 within inputted medical images. Accordingly, the filter component 118 can electronically execute the anatomical detection neural network 604 on each of the plurality of synthetic image variants 204, thereby yielding a plurality of classification labels 606.

As a non-limiting example, the filter component 118 can execute the anatomical detection neural network 604 on the synthetic image variant 204(1), thereby yielding a classification label 606(1). For instance, the synthetic image variant 204(1) can be fed or routed to an input layer of the anatomical detection neural network 604, the synthetic image variant 204(1) can complete a forward pass through one or more hidden layers of the anatomical detection neural network 604, and an output layer of the anatomical detection neural network 604 can compute or calculate the classification label 606(1) based on hidden activation maps produced by the one or more hidden layers of the anatomical detection neural network 604. In various cases, the classification label 606(1) can be any suitable electronic data (e.g., one or more scalars, one or more vectors, one or more matrices, one or more tensors, one or more character strings, or any suitable combination thereof) that can indicate whether or not the synthetic image variant 204(1) depicts or shows the target anatomical structure 602. That is, the classification label 606(1) can indicate or specify whether or not the anatomical detection neural network 604 was able to recognize anything in the synthetic image variant 204(1) as resembling the target anatomical structure 602.

As another non-limiting example, the filter component 118 can execute the anatomical detection neural network 604 on the synthetic image variant 204(n), thereby yielding a classification label 606(n). For instance, the synthetic image variant 204(n) can be fed or routed to the input layer of the anatomical detection neural network 604, the synthetic image variant 204(n) can complete a forward pass through the one or more hidden layers of the anatomical detection neural network 604, and the output layer of the anatomical detection neural network 604 can compute or calculate the classification label 606(n) based on hidden activation maps produced by the one or more hidden layers of the anatomical detection neural network 604. In various cases, the classification label 606(n) can be any suitable electronic data (e.g., one or more scalars, one or more vectors, one or more matrices, one or more tensors, one or more character strings, or any suitable combination thereof) that can indicate whether or not the synthetic image variant 204(n) depicts or shows the target anatomical structure 602. That is, the classification label 606(n) can indicate or specify whether or not the anatomical detection neural network 604 was able to recognize anything in the synthetic image variant 204(n) as resembling the target anatomical structure 602.

In various instances, the classification label 606(1) to the classification label 606(n) can collectively be considered as the plurality of classification labels 606. In various aspects, the filter component 118 can electronically filter the plurality of synthetic image variants 204 based on the plurality of classification labels 606. As a non-limiting example, the filter component 118 can remove from the plurality of synthetic image variants 204 whichever synthetic image variants do not (as inferred by the anatomical detection neural network 604) depict or show the target anatomical structure 602. Accordingly, the plurality of filtered synthetic image variants 502 can lack or omit whichever of the plurality of synthetic image variants 204 that do not contain the target anatomical structure 602. Indeed, if the trained artificial neural network 106 is configured to perform an inferencing task that is clinically related to the target anatomical structure 602, then any synthetic image variants that do not include the target anatomical structure 602 can be considered as inappropriate or unhelpful for re-training or fine-tuning the trained artificial neural network 106.

In various aspects, the anatomical detection neural network 604 can be leveraged to help train the single-image synthesizer neural network 202. Indeed, as mentioned above, the single-image synthesizer neural network 202 can (depending upon its particular internal architecture) be trained using a loss function that includes a reconstruction loss term (e.g., treating the privacy-restricted medical image 104 as a ground-truth) or an adversarial loss term (e.g., in the context of SinGAN). In some instances, however, such loss function can comprise an anatomical structure loss term. As a non-limiting example, the single-image synthesizer neural network 202 can, during its training, produce a predicted or inferred synthetic image variant, which might or might not visually resemble the privacy-restricted medical image 104 depending upon how much training the single-image synthesizer neural network 202 has so far undergone. In various cases, the synthesis component 116 can execute the anatomical detection neural network 604 (which can be already-trained) on the predicted or inferred synthetic image variant, thereby yielding a classification label that indicates whether or not that predicted or inferred synthetic image variant depicts a recognizable version of the target anatomical structure 602. Now, in various aspects, the anatomical structure loss term can be equal to or otherwise based on any suitable error (e.g., MAE, MSE, cross-entropy) between that classification label and a ground-truth classification label indicating that the target anatomical structure is present or has been detected. By including the anatomical structure loss term in training, the single-image synthesizer neural network 202 can become biased toward synthesizing fake images that depict or show the target anatomical structure 602. Equivalently, by including the anatomical structure loss term in training, the single-image synthesizer neural network 202 can become biased away from synthesizing fake images that do not depict or show the target anatomical structure 602.

In any case, the anatomical detection neural network 604 can be leveraged (e.g., during downstream filtration by the filter component 118, or during training by the synthesis component 116), so as to cause the plurality of filtered synthetic image variants 502 to include only fake images that depict the target anatomical structure 602 and thus that would be useful to re-train or fine-tune the trained artificial neural network 106.

Figure 7:
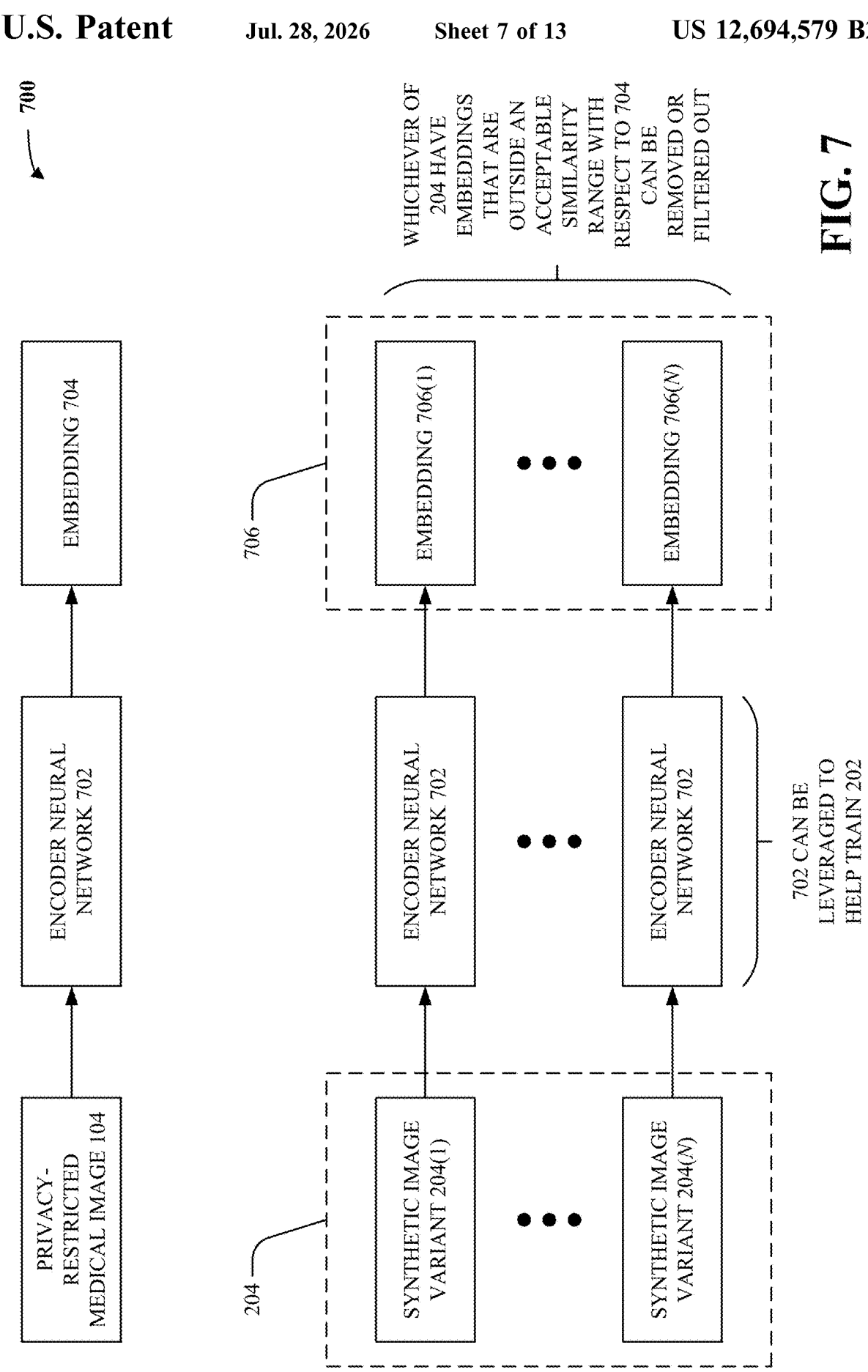

Now, consider FIG. 7. In various embodiments, the filter component 118 can electronically apply embedding filtration to the plurality of synthetic image variants 204.

In various aspects, the filter component 118 can electronically store, electronically maintain, electronically control, or otherwise electronically access an encoder neural network 702. In various aspects, the encoder neural network 702 can exhibit any suitable deep learning internal architecture. Indeed, in various cases, the encoder neural network 702 can have an input layer, one or more hidden layers, and an output layer. In various instances, any of such layers can be coupled together by any suitable interneuron connections or inter-layer connections, such as forward connections, skip connections, or recurrent connections. Furthermore, in various cases, any of such layers can be any suitable types of neural network layers having any suitable learnable or trainable internal parameters. For example, any of such input layer, one or more hidden layers, or output layer can be convolutional layers, whose learnable or trainable parameters can be convolutional kernels. As another example, any of such input layer, one or more hidden layers, or output layer can be dense layers, whose learnable or trainable parameters can be weight matrices or bias values. As still another example, any of such input layer, one or more hidden layers, or output layer can be batch normalization layers, whose learnable or trainable parameters can be shift factors or scale factors. As even another example, any of such input layer, one or more hidden layers, or output layer can be LSTM layers, whose learnable or trainable parameters can be input-state weight matrices or hidden-state weight matrices. As yet another example, any of such input layer, one or more hidden layers, or output layer can be transformer layers, whose learnable or trainable parameters can be single-head or multi-head attention blocks or other weight matrices. Further still, in various cases, any of such layers can be any suitable types of neural network layers having any suitable fixed or non-trainable internal parameters. For example, any of such input layer, one or more hidden layers, or output layer can be non-linearity layers, padding layers, pooling layers, or concatenation layers.

Regardless of its particular internal architecture, the encoder neural network 702 can (as its name suggests) be trained (e.g., in supervised, unsupervised, or reinforcement learning fashion) to encode or compress any inputted medical image into a respective embedding (e.g., a respective latent vector representation). In some cases, the encoder neural network 702 can be the aforementioned encoder model that can be implemented in situations where the single-image synthesizer neural network 202 is derived from a variational autoencoder. Accordingly, the filter component 118 can electronically execute the encoder neural network 702 on each of the plurality of synthetic image variants 204, thereby yielding a plurality of embeddings 706.

As a non-limiting example, the filter component 118 can execute the encoder neural network 702 on the synthetic image variant 204(1), thereby yielding an embedding 706(1). For instance, the synthetic image variant 204(1) can be fed or routed to an input layer of the encoder neural network 702, the synthetic image variant 204(1) can complete a forward pass through one or more hidden layers of the encoder neural network 702, and an output layer of the encoder neural network 702 can compute or calculate the embedding 706(1) based on hidden activation maps produced by the one or more hidden layers of the encoder neural network 702. In various cases, the embedding 706(1) can be one or more scalars, one or more vectors, one or more matrices, or one or more tensors that have fewer (e.g., many orders of magnitude fewer, in some cases) numerical elements than the synthetic image variant 204(1) but that nevertheless represent or encapsulate (e.g., in non-apparent fashion) the visual content of the synthetic image variant 204(1).

As another non-limiting example, the filter component 118 can execute the encoder neural network 702 on the synthetic image variant 204(n), thereby yielding an embedding 706(n). For instance, the synthetic image variant 204(n) can be fed or routed to the input layer of the encoder neural network 702, the synthetic image variant 204(n) can complete a forward pass through the one or more hidden layers of the encoder neural network 702, and the output layer of the encoder neural network 702 can compute or calculate the embedding 706(n) based on hidden activation maps produced by the one or more hidden layers of the encoder neural network 702. So, the embedding 706(n) can be one or more scalars, one or more vectors, one or more matrices, or one or more tensors that have fewer numerical elements than the synthetic image variant 204(n) but that nevertheless represent or encapsulate the visual content of the synthetic image variant 204(n).

In various instances, the embedding 706(1) to the embedding 706(n) can collectively be considered as the plurality of embeddings 706.

Additionally, the filter component 118 can execute the encoder neural network 702 on the privacy-restricted medical image 104 itself, thereby yielding an embedding 704. For instance, the privacy-restricted medical image 104 can be fed or routed to the input layer of the encoder neural network 702, the privacy-restricted medical image 104 can complete a forward pass through the one or more hidden layers of the encoder neural network 702, and the output layer of the encoder neural network 702 can compute or calculate the embedding 704 based on hidden activation maps produced by the one or more hidden layers of the encoder neural network 702. As above, the embedding 704 can be one or more scalars, one or more vectors, one or more matrices, or one or more tensors that have fewer numerical elements than the privacy-restricted medical image 104 but that neverthe-less represent or encapsulate the visual content of the privacy-restricted medical image 104.

Now, in various aspects, the filter component 118 can electronically filter the plurality of synthetic image variants 204 based on the plurality of embeddings 706. Indeed, in some instances, the filter component 118 can remove from the plurality of synthetic image variants 204 whichever synthetic image variants whose embeddings are not within any suitable similarity range of the embedding 704.

As a non-limiting example, for each given embedding of the plurality of embeddings 706, the filter component 118 can compute or calculate a cosine similarity score between that given embedding and the embedding 704. Thus, each of the plurality of synthetic image variants 204 can be consid-ered as having a respective cosine similarity score indicating how similar it is to the privacy-restricted medical image 104. In various aspects, the filter component 118 can remove from the plurality of synthetic image variants 204 any synthetic image variants whose cosine similarity scores fall below any suitable first similarity threshold value. In other words, the plurality of filtered synthetic image variants 502 can lack or omit whichever of the plurality of synthetic image variants 204 that are too different (e.g., as defined by the first similarity threshold value) from the privacy-re-stricted medical image 104. After all, if a synthetic image variant is too unlike the privacy-restricted medical image 104, then such synthetic image variant can be considered as unhelpful for re-training or fine-tuning the trained artificial neural network 106. Moreover, in some aspects, the filter component 118 can remove from the plurality of synthetic image variants 204 any synthetic image variants whose cosine similarity scores are above any suitable second similarity threshold value, where the second similarity threshold value is greater than the first similarity threshold value. In other words, the plurality of filtered synthetic image variants 502 can lack or omit whichever of the plurality of synthetic image variants 204 that are too similar (e.g., as defined by the second similarity threshold value) to the privacy-restricted medical image 104. After all, if a synthetic image variant is too much like the privacy-re-stricted medical image 104, then such synthetic image variant might be subject to whatever privacy laws or regu-lations that are applicable to the privacy-restricted medical image 104 and thus might not be permissible for re-training or fine-tuning the trained artificial neural network 106. In this non-limiting example, the first and second similarity thresholds can be considered as defining an acceptable similarity range, where any synthetic image variant falling outside of that acceptable similarity range can be removed from the plurality of synthetic image variants 204.

As another non-limiting example, for each given embed-ding of the plurality of embeddings 706, the filter component

118 can compute or calculate a Euclidean distance between that given embedding and the embedding 704. Thus, each of the plurality of synthetic image variants 204 can be consid-ered as having a respective Euclidean distance indicating how far it is from the privacy-restricted medical image 104. In various aspects, the filter component 118 can remove from the plurality of synthetic image variants 204 any synthetic image variants whose Euclidean distances are above any suitable first distance threshold value. In other words, the plurality of filtered synthetic image variants 502 can lack or omit whichever of the plurality of synthetic image variants 204 that are too far (e.g., as defined by the first distance threshold value) from the privacy-restricted medical image 104. After all, if a synthetic image variant is too unlike the privacy-restricted medical image 104, then such synthetic image variant can be considered as unhelpful for re-training or fine-tuning the trained artificial neural network 106. Moreover, in some aspects, the filter compo-nent 118 can remove from the plurality of synthetic image variants 204 any synthetic image variants whose Euclidean distances fall below any suitable second distance threshold value, where the second distance threshold value is lesser than the first distance threshold value. In other words, the plurality of filtered synthetic image variants 502 can lack or omit whichever of the plurality of synthetic image variants 204 that are too close (e.g., as defined by the second distance threshold value) to the privacy-restricted medical image 104. After all, if a synthetic image variant is too much like the privacy-restricted medical image 104, then such syn-thetic image variant might be subject to whatever privacy laws or regulations that are applicable to the privacy-restricted medical image 104 and thus might not be permis-sible for re-training or fine-tuning the trained artificial neural network 106. In this non-limiting example, the first and second distance thresholds can be considered as defining an acceptable similarity range, where any synthetic image variant falling outside of that acceptable similarity range can be removed from the plurality of synthetic image variants 204.

In various aspects, the encoder neural network 702 can be leveraged to help train the single-image synthesizer neural network 202. Indeed, as mentioned above, the single-image synthesizer neural network 202 can (depending upon its particular internal architecture) be trained using a loss function that includes a reconstruction loss term, an adver-sarial loss term, or an anatomical structure loss term. In some instances, however, such loss function can comprise an embedding loss term. As a non-limiting example, the single-image synthesizer neural network 202 can, during its train-ing, produce a predicted or inferred synthetic image variant, which might or might not visually resemble the privacy-restricted medical image 104 depending upon how much training the single-image synthesizer neural network 202 has so far undergone. In various cases, the synthesis component 116 can execute the encoder neural network 702 (which can be already-trained) on the predicted or inferred synthetic image variant, thereby yielding an embedding that latently represents the visual content of that predicted or inferred synthetic image variant. Now, in various aspects, the embed-ding loss term can be equal to or otherwise based on any suitable error (e.g., MAE, MSE, cross-entropy) between that embedding and the embedding 704 (which can be consid-ered as a ground-truth). In some cases, such error can be additively offset by any suitable positive scalars correspond-ing to the aforementioned acceptable similarity range, such that minimization of the embedding loss term causes the embeddings of predicted or inferred synthetic image variants to converge or fall into that acceptable similarity range. In other words, by including the embedding loss term in training, the single-image synthesizer neural network 202 can become biased toward synthesizing fake images whose embeddings are not too different from, and yet simultaneously are not too similar to, the embedding 704 of the privacy-restricted medical image 104.

In any case, the encoder neural network 702 can be leveraged (e.g., during downstream filtration by the filter component 118, or during training by the synthesis component 116), so as to cause the plurality of filtered synthetic image variants 502 to include only fake images whose visual contents are within an acceptable similarity range of that of the privacy-restricted medical image 104, and thus that would be useful to re-train or fine-tune the trained artificial neural network 106 without being subject to the privacy laws or regulations of the privacy-restricted medical image 104.

Figure 8:
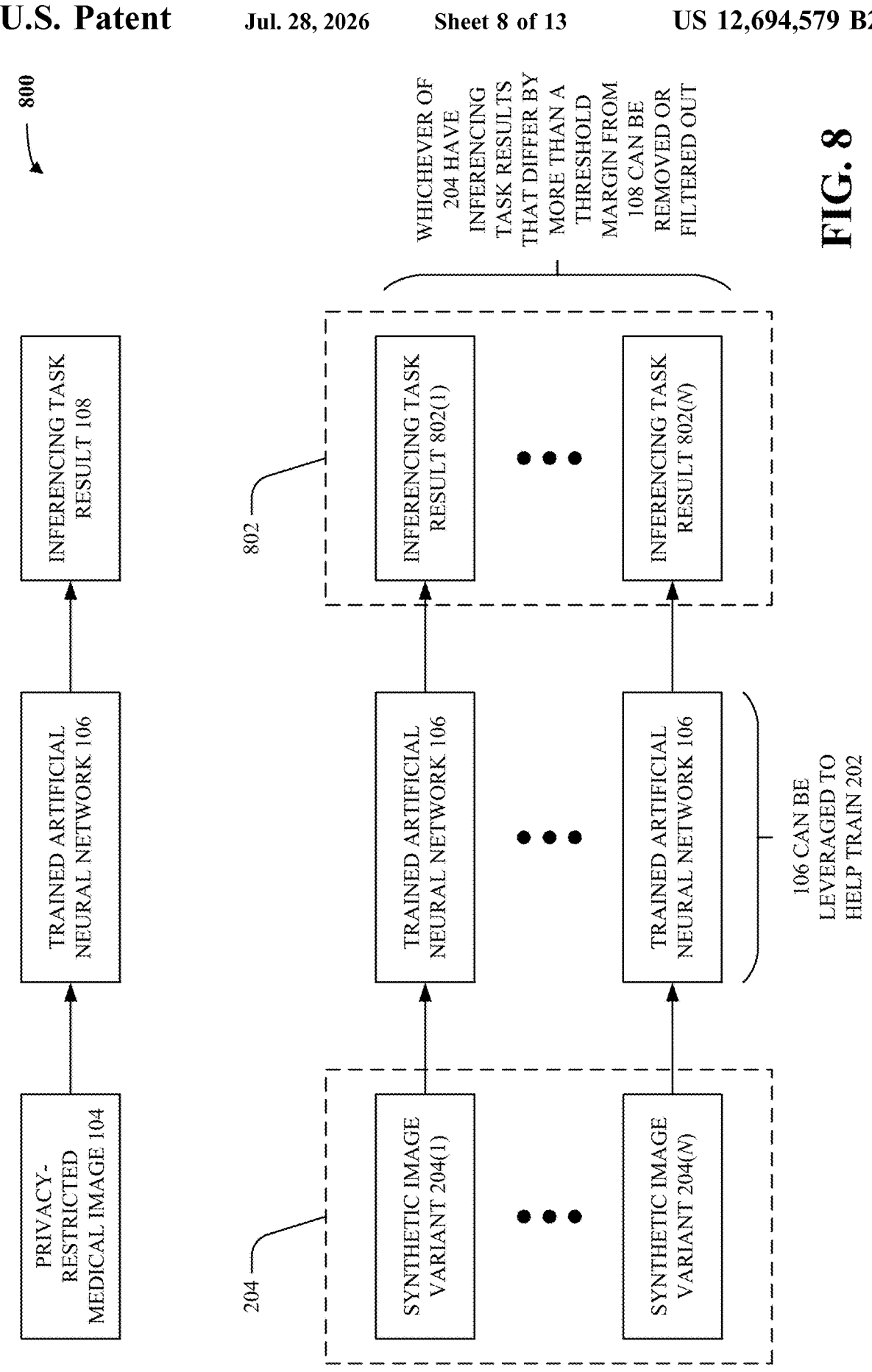

Next, consider FIG. 8. In various embodiments, as mentioned above, the trained artificial neural network 106 can be executed on the privacy-restricted medical image 104, thereby yielding an inferencing task result 108. In various aspects, the filter component 118 can electronically execute the trained artificial neural network 106 on each of the plurality of synthetic image variants 204, thereby yielding a plurality of inferencing task results 802.

As a non-limiting example, the filter component 118 can execute the trained artificial neural network 106 on the synthetic image variant 204(1), thereby yielding an inferencing task result 802(1). For instance, the synthetic image variant 204(1) can be fed or routed to the input layer of the trained artificial neural network 106, the synthetic image variant 204(1) can complete a forward pass through the one or more hidden layers of the trained artificial neural network 106, and the output layer of the trained artificial neural network 106 can compute or calculate the inferencing task result 802(1) based on hidden activation maps produced by the one or more hidden layers of the trained artificial neural network 106. In various cases, the inferencing task result 802(1) can be whatever predicted or inferred result (e.g., predicted or inferred classification label, predicted or inferred segmentation mask, predicted or inferred regression output) that the trained artificial neural network 106 believes should correspond to the synthetic image variant 204(1).

As another non-limiting example, the filter component 118 can execute the trained artificial neural network 106 on the synthetic image variant 204(n), thereby yielding an inferencing task result 802(n). For instance, the synthetic image variant 204(n) can be fed or routed to the input layer of the trained artificial neural network 106, the synthetic image variant 204(n) can complete a forward pass through the one or more hidden layers of the trained artificial neural network 106, and the output layer of the trained artificial neural network 106 can compute or calculate the inferencing task result 802(n) based on hidden activation maps produced by the one or more hidden layers of the trained artificial neural network 106. In various cases, the inferencing task result 802(n) can be whatever predicted or inferred result (e.g., predicted or inferred classification label, predicted or inferred segmentation mask, predicted or inferred regression output) that the trained artificial neural network 106 believes should correspond to the synthetic image variant 204(n).

In various instances, the inferencing task result 802(1) to the inferencing task result 802(n) can collectively be considered as the plurality of inferencing task results 802.

Now, in various aspects, the filter component 118 can electronically filter the plurality of synthetic image variants 204 based on the plurality of inferencing task results 802. Indeed, in some instances, the filter component 118 can remove from the plurality of synthetic image variants 204 whichever synthetic image variants whose inferencing task results differ by more than any suitable threshold margin from the inferencing task result 108.

As a non-limiting example, for each given inferencing task result of the plurality of inferencing task results 802, the filter component 118 can compute or calculate an error (e.g., MAE, MSE, cross-entropy) between that given inferencing task result and the inferencing task result 108. Thus, each of the plurality of synthetic image variants 204 can be considered as having a respective inferencing task error. In various aspects, the filter component 118 can remove from the plurality of synthetic image variants 204 any synthetic image variants whose inferencing task errors are above any suitable threshold value. In other words, the plurality of filtered synthetic image variants 502 can lack or omit whichever of the plurality of synthetic image variants 204 whose inferencing task results are too different (e.g., as defined by the threshold value) from that of the privacy-restricted medical image 104. After all, if the trained artificial neural network 106 produces a different inferencing task result for a given synthetic image variant than it produced for the privacy-restricted medical image 104, then such given synthetic image variant can be considered missing task-dispositive visual content that is within the privacy-restricted medical image 104. Accordingly, such given synthetic image variant can be considered as unhelpful for re-training or fine-tuning the trained artificial neural network 106.

In various aspects, the trained artificial neural network 106 can be leveraged to help train the single-image synthesizer neural network 202. Indeed, as mentioned above, the single-image synthesizer neural network 202 can (depending upon its particular internal architecture) be trained using a loss function that includes a reconstruction loss term, an adversarial loss term, an anatomical structure loss term, or an embedding loss term. In some instances, however, such loss function can comprise an inferencing task loss term. As a non-limiting example, the single-image synthesizer neural network 202 can, during its training, produce a predicted or inferred synthetic image variant, which might or might not visually resemble the privacy-restricted medical image 104 depending upon how much training the single-image synthesizer neural network 202 has so far undergone. In various cases, the synthesis component 116 can execute the trained artificial neural network 106 (which can be already-trained) on the predicted or inferred synthetic image variant, thereby yielding an inferencing task result for that predicted or inferred synthetic image variant. Now, in various aspects, the inferencing task loss term can be equal to or otherwise based on any suitable error (e.g., MAE, MSE, cross-entropy) between that inferencing task result and the inferencing task result 108 (which can be considered as a sort of ground-truth with respect to the single-image synthesizer neural network 202, even if the inferencing task result 108 is actually wrong or incorrect with respect to the privacy-restricted medical image 104). Accordingly, by including the inferencing task loss term in training, the single-image synthesizer neural network 202 can become biased toward synthesizing fake images whose inferencing task results are the same as or similar to the inferencing task result 108 of the privacy-restricted medical image 104.

In any case, the trained artificial neural network 106 can be leveraged (e.g., during downstream filtration by the filter component 118, or during training by the synthesis component 116), so as to cause the plurality of filtered synthetic image variants 502 to include only fake images whose visual contents are treated by the trained artificial neural network 106 in the same way as the visual content of the privacy-restricted medical image 104.

Figure 9:
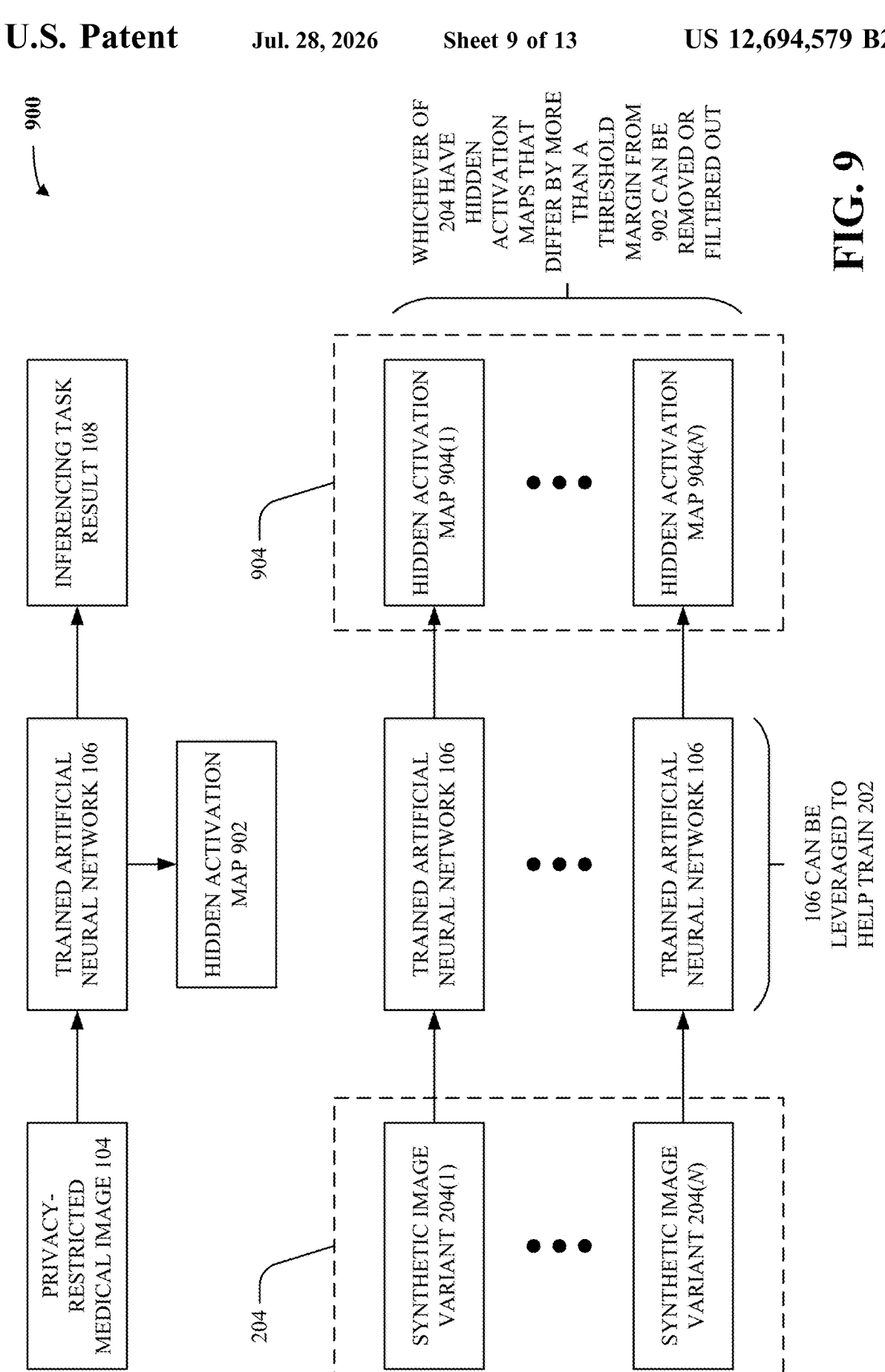

Now, consider FIG. 9. In various embodiments, as mentioned above, the trained artificial neural network 106 can be executed on the privacy-restricted medical image 104, thereby yielding an inferencing task result 108. During such execution, any specific hidden layer of the trained artificial neural network 106 can produce a hidden activation map 902. In various aspects, the filter component 118 can electronically execute the trained artificial neural network 106 on each of the plurality of synthetic image variants 204, thereby yielding a plurality of hidden activation maps 904.

As a non-limiting example, the filter component 118 can execute the trained artificial neural network 106 on the synthetic image variant 204(1), and the specific hidden layer of the trained artificial neural network 106 can produce a hidden activation map 904(1) during such execution. In various aspects, the hidden activation map 904(1) can be considered as an intermediate computational result (e.g., one or more scalars, one or more vectors, one or more matrices, one or more tensors, or any suitable combination thereof) that is internally computed by the trained artificial neural network 106 during the forward pass of the synthetic image variant 204(1).

As another non-limiting example, the filter component 118 can execute the trained artificial neural network 106 on the synthetic image variant 204(n), and the specific hidden layer of the trained artificial neural network 106 can produce a hidden activation map 904(n) during such execution. As above, the hidden activation map 904(n) can be considered as an intermediate computational result that is internally computed by the trained artificial neural network 106 during the forward pass of the synthetic image variant 204(n).

In various instances, the hidden activation map 904(1) to the hidden activation map 904(n) can collectively be considered as the plurality of hidden activation maps 904.

Now, in various aspects, the filter component 118 can electronically filter the plurality of synthetic image variants 204 based on the plurality of hidden activation maps 904. Indeed, in some instances, the filter component 118 can remove from the plurality of synthetic image variants 204 whichever synthetic image variants whose hidden activation maps differ by more than any suitable threshold margin from the hidden activation map 902.

As a non-limiting example, for each given hidden activation map of the plurality of hidden activation maps 904, the filter component 118 can compute or calculate an error (e.g., MAE, MSE, cross-entropy) between that given hidden activation map and the hidden activation map 902. Thus, each of the plurality of synthetic image variants 204 can be considered as having a respective hidden map error. In various aspects, the filter component 118 can remove from the plurality of synthetic image variants 204 any synthetic image variants whose hidden map errors are above any suitable threshold value. In other words, the plurality of filtered synthetic image variants 502 can lack or omit whichever of the plurality of synthetic image variants 204 whose hidden activation maps are too different (e.g., as defined by the threshold value) from that of the privacy-restricted medical image 104. After all, if the trained artificial neural network 106 produces a different hidden activation maps for a given synthetic image variant than it produced for the privacy-restricted medical image 104, then such given synthetic image variant can be considered missing task-relevant visual content that is within the privacy-restricted medical image 104. Accordingly, such given synthetic image variant can be considered as unhelpful for re-training or fine-tuning the trained artificial neural network 106.

In various aspects, the trained artificial neural network 106 can be leveraged to help train the single-image synthesizer neural network 202. Indeed, as mentioned above, the single-image synthesizer neural network 202 can (depending upon its particular internal architecture) be trained using a loss function that includes a reconstruction loss term, an adversarial loss term, an anatomical structure loss term, an embedding loss term, or an inferencing task loss term. In some instances, however, such loss function can comprise a hidden map loss term. As a non-limiting example, the single-image synthesizer neural network 202 can, during its training, produce a predicted or inferred synthetic image variant, which might or might not visually resemble the privacy-restricted medical image 104 depending upon how much training the single-image synthesizer neural network 202 has so far undergone. In various cases, the synthesis component 116 can execute the trained artificial neural network 106 (which can be already-trained) on the predicted or inferred synthetic image variant, thereby causing the specific hidden layer of the trained artificial neural network 106 to produce a hidden activation map for that predicted or inferred synthetic image variant. Now, in various aspects, the hidden map loss term can be equal to or otherwise based on any suitable error (e.g., MAE, MSE, cross-entropy) between that hidden activation map and the hidden activation map 902 (which can be considered as a sort of ground-truth). Accordingly, by including the hidden map loss term in training, the single-image synthesizer neural network 202 can become biased toward synthesizing fake images whose hidden activation maps are the same as or similar to the hidden activation map 902 of the privacy-restricted medical image 104.

In any case, the trained artificial neural network 106 can be leveraged (e.g., during downstream filtration by the filter component 118, or during training by the synthesis component 116), so as to cause the plurality of filtered synthetic image variants 502 to include only fake images whose visual contents are treated by the trained artificial neural network 106 in the same way as the visual content of the privacy-restricted medical image 104.

In various cases, the filter component 118 can apply any other suitable type of filtration to the plurality of synthetic image variants 204. As a non-limiting example, the filter component 118 can compute any suitable image property or metadata (e.g., pixel or voxel mean; pixel or voxel standard deviation, brightness level, contrast level) for each of the plurality of synthetic image variants 204, and the filter component 118 can remove any synthetic image variants whose computed property or metadata does not satisfy any suitable threshold. As above, such filtration can, in some cases, be implemented as an additional loss term (e.g., image property loss term) during training of the single-image synthesizer neural network 202, so as to bias the single-image synthesizer neural network 202 toward creating fake images whose properties or metadata satisfy the threshold.

In various embodiments, the plurality of filtered synthetic image variants 502 can be considered as containing fake images that visually resemble or are visually reminiscent of the privacy-restricted medical image 104, but that are nevertheless sufficiently visually different from the privacy-restricted medical image 104 so as to not be subject to applicable privacy laws or regulations. Accordingly, the fine-tune component 120 can, in various aspects, electronically cause the trained artificial neural network 106 to be re-trained or fine-tuned on the plurality of filtered synthetic image variants 502 (and not on the privacy-restricted medical image 104 itself).

As a non-limiting example, the fine-tune component 120 can electronically share the plurality of filtered synthetic image variants 502 with a computing device that is responsible for re-training or fine-tuning the trained artificial neural network 106, along with an instruction to begin or commence re-training.

As another non-limiting example, the fine-tune component 120 can, in some cases, itself re-train or fine-tune the trained artificial neural network 106 using the plurality of filtered synthetic image variants 502.

Figure 10:
FIG. 10 illustrates an example, non-limiting block diagram showing how a machine learning model can be fine-tuned using filtered synthetic image variants in accordance with one or more embodiments described herein.

FIG. 10 illustrates an example, non-limiting block diagram 1000 showing how the trained artificial neural network 106 can be fine-tuned using the plurality of filtered synthetic image variants 502 in accordance with one or more embodiments described herein.

In various aspects, note that, prior to beginning training, the trainable internal parameters (e.g., convolutional kernels, weight matrices, bias values) of the trained artificial neural network 106 can be not re-initialized. After all, such re-initialization would cause the trained artificial neural network 106 to forget all its prior learning, which can be undesirable.

In various embodiments, there can be a synthetic image variant 1002 and a ground-truth annotation 1004. In various aspects, the synthetic image variant 1002 can be any of the plurality of filtered synthetic image variants 502. In various instances, the ground-truth annotation 1004 can be whatever correct or accurate inferencing task result (e.g., correct or accurate classification label, correct or accurate segmentation mask, correct or accurate regression output) that is known or deemed to correspond to the synthetic image variant 1002 and thus to the privacy-restricted medical image 104. Note that the ground-truth annotation 1004 can be common to all of the plurality of filtered synthetic image variants 502, since each of the plurality of filtered synthetic image variants 502 can be a version of the privacy-restricted medical image 104. Additionally, note that the ground-truth annotation 1004 can be different from the inferencing task result 108 (e.g., in some cases, the inferencing task result 108 can be incorrect or inaccurate).

In any case, the trained artificial neural network 106 can be executed on the synthetic image variant 1002, thereby causing the trained artificial neural network 106 to produce an inferencing task result 1006. In various aspects, an error 1008 (e.g., MAE, MSE, cross-entropy) between the inferencing task result 1006 and the ground-truth annotation 1004 can be computed. In various instances, the trainable internal parameters of the trained artificial neural network 106 can be incrementally updated via backpropagation (e.g., stochastic gradient descent) based on the error 1008.

In various cases, such execution-and-update procedure can be repeated any suitable number of times (e.g., for each of the plurality of filtered synthetic image variants 502). This can ultimately cause the trainable internal parameters of the trained artificial neural network 106 to become iteratively optimized for accurately performing the inferencing task result on images that look like the privacy-restricted medical image 104, notwithstanding that the privacy-restricted medical image 104 itself is not used to re-train or fine-tune the trained artificial neural network 106. In various aspects, any suitable training batch sizes, any suitable error/loss functions, or any suitable training termination criteria can be utilized during such re-training or fine-tuning.

Although the herein disclosure mainly describes the trained artificial neural network 106 as being re-trained or fine-tuned in supervised fashion, this is a mere non-limiting example for case of explanation and illustration. In various embodiments, any other suitable training paradigms can be used to re-train or fine-tune the trained artificial neural network 106, such as unsupervised training or reinforcement learning, any of which may be federated or unfederated.

It should be appreciated that various embodiments described herein can be applied to any suitable number of privacy-restricted medical images (e.g., for each privacy-restricted medical image that is desired, a separate instantiation of the single-image synthesizer neural network 202 can be trained).

Although various embodiments described herein involve the single-image synthesizer neural network 202 synthesizing entireties of fake images, this is a mere non-limiting example for case of explanation and illustration. In some cases, the single-image synthesizer neural network 202 can instead be configured to synthesize less than entire fake images.

As a non-limiting example, suppose that the privacy-restricted medical image 104 is an x-by-y pixel array. In some embodiments, the single-image synthesizer neural network 202 can be configured to synthesize x-by-y pixel arrays that visually resemble the privacy-restricted medical image 104. Thus, a synthetic image variant in such case can be whatever final output is produced by the single-image synthesizer neural network 202. However, in other embodiments, the single-image synthesizer neural network 202 can instead be configured to synthesize an $(i_{upper}-i_{lower}+1)$-by-$(j_{upper}-j_{lower}+1)$ pixel array, for any suitable positive integers $i_{lower} \leq i_{upper} \geq x$ and $j_{lower} \leq j_{upper} \leq y$. In such case, that pixel array can be synthetic content that resembles whatever visual content is shown between the $i_{lower}$-th and $i_{upper}$-th rows of the privacy-restricted medical image 104 and between the $j_{lower}$-th and $j_{upper}$-th columns of the privacy-restricted medical image 104. Thus, a synthetic image variant in such case can be considered as the result obtained by superimposing that $(i_{upper}-i_{lower}+1)$-by-$(j_{upper}-j_{lower}+1)$ pixel array over corresponding rows and columns of the privacy-restricted medical image 104. In other words, the privacy-restricted medical image 104 can be considered as having a region of interest between its $i_{lower}$-th and $i_{upper}$-th rows and its $j_{lower}$-th and $j_{upper}$-th columns, and the single-image synthesizer neural network 202 can be configured to synthesize fake versions or variants of only that region of interest, rather than synthesizing fake versions or variations of the entirety of the privacy-restricted medical image 104. This can help to reduce a computational footprint of the single-image synthesizer neural network 202.

FIG. 11 illustrates a flow diagram of an example, non-limiting computer-implemented method 1100 that can facilitate medical image privacy preservation via image synthesis and filtration in accordance with one or more embodiments described herein. In various cases, the privacy system 102 can facilitate the computer-implemented method 1100.

In various embodiments, act 1102 can include accessing, by at least one of one or more devices (e.g., via 114) operatively coupled to a processor (e.g., 110), a medical image (e.g., 104) for which a first artificial neural network (e.g., 106) has produced an inferencing task result. (e.g., 108).

In various aspects, act 1104 can include training, by at least one of the one or more devices (e.g., via 116), a second artificial neural network (e.g., 202) on the medical image to perform image synthesis.

In various instances, act 1106 can include generating, by at least one of the one or more devices (e.g., via 116) and via execution of the second artificial neural network post-training, a set of synthetic variants (e.g., 204) of the medical image.

In various cases, act 1108 can include fine-tuning, by at least one of the one or more devices (e.g., via 120), the first artificial neural network using at least some (e.g., 502) of the set of synthetic variants of the medical image rather than using the medical image (e.g., such fine-tuning can include or involve retraining the first artificial neural network without re-initializing its internal parameters, such as described with respect to FIG. 10).

Although not explicitly shown in FIG. 11, the second artificial neural network can be: a generator of a single-image generative adversarial network; a single image denoising diffusion model; or a variational autoencoder.

Although not explicitly shown in FIG. 11, the medical image can depict a target anatomical structure (e.g., 602), and the computer-implemented method 1100 can comprise: identifying, by at least one of the one or more devices (e.g., via 118), within the set of synthetic variants of the medical image, and via execution of a third artificial neural network (e.g., 604) that is trained to classify or detect anatomical structures in inputted images, one or more synthetic variants of the medical image that do not depict the target anatomical structure; and removing, by at least one of the one or more devices (e.g., via 118), those one or more synthetic variants of the medical image from the set of synthetic variants of the medical image, such that those one or more synthetic variants of the medical image are not used to fine-tune the first artificial neural network.

Although not explicitly shown in FIG. 11, the medical image can correspond to an embedding (e.g., 704), and the computer-implemented method 1100 can comprise: identifying, by at least one of the one or more devices (e.g., via 118), within the set of synthetic variants of the medical image, and via execution of a third artificial neural network (e.g., 702) that is trained to create embeddings for inputted images, one or more synthetic variants of the medical image whose embeddings (e.g., 706) differ by less than a first threshold margin from the embedding of the medical image or by more than a second threshold margin from the embedding of the medical image, wherein the first threshold margin can be less than the second threshold margin; and removing, by at least one of the one or more devices (e.g., via 118), those one or more synthetic variants of the medical image from the set of synthetic variants of the medical image, such that those one or more synthetic variants of the medical image are not used to fine-tune the first artificial neural network.

Although not explicitly shown in FIG. 11, the computer-implemented method 1100 can comprise: generating, by at least one of the one or more devices (e.g., via 118) and via execution of the first artificial neural network, a set of inferencing task results (e.g., 802) respectively corresponding to the set of synthetic variants of the medical image; identifying, by at least one of the one or more devices (e.g., via 118) and within the set of synthetic variants of the medical image, one or more synthetic variants of the medical image whose inferencing task results differ by more than a threshold margin from the inferencing task result; and removing, by at least one of the one or more devices (e.g., via 118), those one or more synthetic variants of the medical image from the set of synthetic variants of the medical image, such that those one or more synthetic variants of the medical image are not used to fine-tune the first artificial neural network.

Although not explicitly shown in FIG. 11, the first artificial neural network can have produced a first hidden activation map (e.g., 902) for the medical image, and the computer-implemented method 1100 can comprise: generating, by at least one of the one or more devices (e.g., via 118) and via execution of the first artificial neural network, a set of hidden activation maps (e.g., 904) respectively corresponding to the set of synthetic variants of the medical image; identifying, by at least one of the one or more devices (e.g., via 118) and within the set of synthetic variants of the medical image, one or more synthetic variants of the medical image whose hidden activation maps differ by more than a threshold margin from the first hidden activation map; and removing, by at least one of the one or more devices (e.g., via 118), those one or more synthetic variants of the medical image from the set of synthetic variants of the medical image, such that those one or more synthetic variants of the medical image are not used to fine-tune the first artificial neural network.

Although not explicitly shown in FIG. 11, the second artificial neural network can be configured to synthesize a region of interest within the medical image rather than an entirety of the medical image.

Although not explicitly shown in FIG. 11, a training loss of the second artificial neural network can be based on: anatomical structure filtration; embedding filtration; inferencing task result filtration; or hidden activation map filtration.

Although the herein disclosure mainly describes various embodiments that involve leveraging the plurality of filtered synthetic image variants 502 to retrain or fine-tune the trained artificial neural network 106, these are mere non-limiting examples for case of explanation and illustration. It should be appreciated that various embodiments described herein can electronically transmit the plurality of filtered synthetic image variants 502 to any other suitable computing devices to be used or leveraged for any other suitable purposes. Note that, in some cases, each of the plurality of filtered synthetic image variants 502 can be tagged, marked, flagged, linked, or otherwise associated with any suitable non-private metadata regarding the medical patient that is depicted in the privacy-restricted medical image 104. Any private or identifying metadata regarding the medical patient (e.g., name, address, social security number) can be omitted or filtered out, whereas any non-private or non-identifying metadata regarding the medical patient (e.g., age, gender, body mass index, occupation) can be preserved and appended to each of the plurality of filtered synthetic image variants 502. Such non-private or non-identifying metadata can be considered as valuable context for the plurality of filtered synthetic image variants 502. Indeed, in some cases, such non-private or non-identifying metadata can be treated as additional or supplemental inputs that are receivable by the trained artificial neural network 106, or that can be otherwise considered or taken into account for whatever downstream purposes or uses the plurality of filtered synthetic image variants 502 are intended.

In various instances, machine learning algorithms or models can be implemented in any suitable way to facilitate any suitable aspects described herein. To facilitate some of the above-described machine learning aspects of various embodiments, consider the following discussion of artificial intelligence (AI). Various embodiments described herein can employ artificial intelligence to facilitate automating one or more features or functionalities. The components can employ various AI-based schemes for carrying out various embodiments/examples disclosed herein. In order to provide for or aid in the numerous determinations (e.g., determine, ascertain, infer, calculate, predict, prognose, estimate, derive, forecast, detect, compute) described herein, components described herein can examine the entirety or a subset of the data to which it is granted access and can provide for reasoning about or determine states of the system or environment from a set of observations as captured via events or data. Determinations can be employed to identify a specific context or action, or can generate a probability distribution over states, for example. The determinations can be probabilistic; that is, the computation of a probability distribution over states of interest based on a consideration of data and events. Determinations can also refer to techniques employed for composing higher-level events from a set of events or data.

Such determinations can result in the construction of new events or actions from a set of observed events or stored event data, whether or not the events are correlated in close temporal proximity, and whether the events and data come from one or several event and data sources. Components disclosed herein can employ various classification (explicitly trained (e.g., via training data) as well as implicitly trained (e.g., via observing behavior, preferences, historical information, receiving extrinsic information, and so on)) schemes or systems (e.g., support vector machines, neural networks, expert systems, Bayesian belief networks, fuzzy logic, data fusion engines, and so on) in connection with performing automatic or determined action in connection with the claimed subject matter. Thus, classification schemes or systems can be used to automatically learn and perform a number of functions, actions, or determinations.

A classifier can map an input attribute vector, $z=(z_1, z_2, z_3, z_4, z_n)$, to a confidence that the input belongs to a class, as by $f(z)=confidence$ (class). Such classification can employ a probabilistic or statistical-based analysis (e.g., factoring into the analysis utilities and costs) to determinate an action to be automatically performed. A support vector machine (SVM) can be an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, or probabilistic classification models providing different patterns of independence, any of which can be employed. Classification as used herein also is inclusive of statistical regression that is utilized to develop models of priority.

Figure 12:
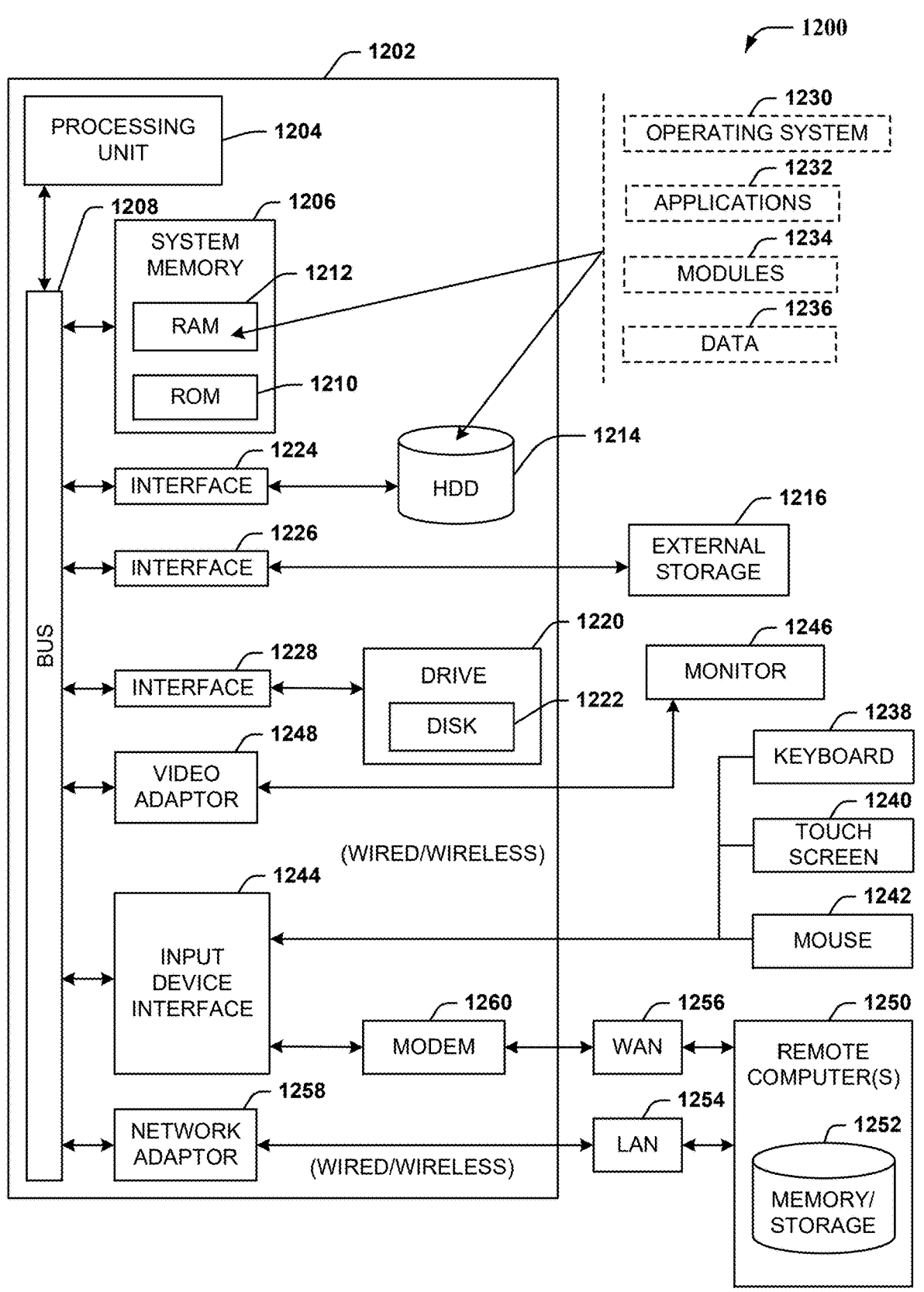
FIG. 12 illustrates a block diagram of an example, non-limiting operating environment in which one or more embodiments described herein can be facilitated.

In order to provide additional context for various embodiments described herein, FIG. 12 and the following discussion are intended to provide a brief, general description of a suitable computing environment 1200 in which the various embodiments of the embodiment described herein can be implemented. While the embodiments have been described above in the general context of computer-executable instructions that can run on one or more computers, those skilled in the art will recognize that the embodiments can be also implemented in combination with other program modules or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multi-processor computer systems, minicomputers, mainframe computers, Internet of Things (IoT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 12, the example environment 1200 for implementing various embodiments of the aspects described herein includes a computer 1202, the computer 1202 including a processing unit 1204, a system memory 1206 and a system bus 1208. The system bus 1208 couples system components including, but not limited to, the system memory 1206 to the processing unit 1204. The processing unit 1204 can be any of various commercially available processors. Dual microprocessors and other multi-processor architectures can also be employed as the processing unit 1204.

The system bus 1208 can be any of several types of bus structure that can further interconnect to a memory bus (with or without a memory controller), a peripheral bus, and a local bus using any of a variety of commercially available bus architectures. The system memory 1206 includes ROM 1210 and RAM 1212. A basic input/output system (BIOS) can be stored in a non-volatile memory such as ROM, erasable programmable read only memory (EPROM), EEPROM, which BIOS contains the basic routines that help to transfer information between elements within the computer 1202, such as during startup. The RAM 1212 can also include a high-speed RAM such as static RAM for caching data.

The computer 1202 further includes an internal hard disk drive (HDD) 1214 (e.g., EIDE, SATA), one or more external storage devices 1216 (e.g., a magnetic floppy disk drive (FDD) 1216, a memory stick or flash drive reader, a memory card reader, etc.) and a drive 1220, e.g., such as a solid state drive, an optical disk drive, which can read or write from a disk 1222, such as a CD-ROM disc, a DVD, a BD, etc. Alternatively, where a solid state drive is involved, disk 1222 would not be included, unless separate. While the internal HDD 1214 is illustrated as located within computer 1202, the internal HDD 1214 can also be configured for external use in a suitable chassis (not shown). Additionally, while not shown in environment 1200, a solid state drive (SSD) could be used in addition to, or in place of, an HDD 1214. The HDD 1214, external storage device(s) 1216 and drive 1220 can be connected to the system bus 1208 by an HDD interface 1224, an external storage interface 1226 and a drive interface 1228, respectively. The interface 1224 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 1202, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 1212, including an operating system 1230, one or more application programs 1232, other program modules 1234 and program data 1236. All or portions of the operating system, applications, modules, or data can also be cached in the RAM 1212. The systems and methods described herein can be implemented utilizing various commercially available operating systems or combinations of operating systems.

Computer 1202 can optionally comprise emulation technologies. For example, a hypervisor (not shown) or other intermediary can emulate a hardware environment for operating system 1230, and the emulated hardware can optionally be different from the hardware illustrated in FIG. 12. In such an embodiment, operating system 1230 can comprise one virtual machine (VM) of multiple VMs hosted at computer 1202. Furthermore, operating system 1230 can provide runtime environments, such as the Java runtime environment or the .NET framework, for applications 1232. Runtime environments are consistent execution environments that allow applications 1232 to run on any operating system that includes the runtime environment. Similarly, operating system 1230 can support containers, and applications 1232 can be in the form of containers, which are lightweight, standalone, executable packages of software that include, e.g., code, runtime, system tools, system libraries and settings for an application.

Further, computer 1202 can be enable with a security module, such as a trusted processing module (TPM). For instance with a TPM, boot components hash next in time boot components, and wait for a match of results to secured values, before loading a next boot component. This process can take place at any layer in the code execution stack of computer 1202, e.g., applied at the application execution level or at the operating system (OS) kernel level, thereby enabling security at any level of code execution.

A user can enter commands and information into the computer 1202 through one or more wired/wireless input devices, e.g., a keyboard 1238, a touch screen 1240, and a pointing device, such as a mouse 1242. Other input devices (not shown) can include a microphone, an infrared (IR) remote control, a radio frequency (RF) remote control, or other remote control, a joystick, a virtual reality controller or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 1204 through an input device interface 1244 that can be coupled to the system bus 1208, but can be connected by other interfaces, such as a parallel port, an IEEE 1394 serial port, a game port, a USB port, an IR interface, a BLUETOOTH® interface, etc.

A monitor 1246 or other type of display device can be also connected to the system bus 1208 via an interface, such as a video adapter 1248. In addition to the monitor 1246, a computer typically includes other peripheral output devices (not shown), such as speakers, printers, etc.

The computer 1202 can operate in a networked environment using logical connections via wired or wireless communications to one or more remote computers, such as a remote computer(s) 1250. The remote computer(s) 1250 can be a workstation, a server computer, a router, a personal computer, portable computer, microprocessor-based entertainment appliance, a peer device or other common network node, and typically includes many or all of the elements described relative to the computer 1202, although, for purposes of brevity, only a memory/storage device 1252 is illustrated. The logical connections depicted include wired/wireless connectivity to a local area network (LAN) 1254 or larger networks, e.g., a wide area network (WAN) 1256. Such LAN and WAN networking environments are commonplace in offices and companies, and facilitate enterprise-wide computer networks, such as intranets, all of which can connect to a global communications network, e.g., the Internet.

When used in a LAN networking environment, the computer 1202 can be connected to the local network 1254 through a wired or wireless communication network interface or adapter 1258. The adapter 1258 can facilitate wired or wireless communication to the LAN 1254, which can also include a wireless access point (AP) disposed thereon for communicating with the adapter 1258 in a wireless mode.

When used in a WAN networking environment, the computer 1202 can include a modem 1260 or can be connected to a communications server on the WAN 1256 via other means for establishing communications over the WAN 1256, such as by way of the Internet. The modem 1260, which can be internal or external and a wired or wireless device, can be connected to the system bus 1208 via the input device interface 1244. In a networked environment, program modules depicted relative to the computer 1202 or portions thereof, can be stored in the remote memory/ storage device 1252. It will be appreciated that the network connections shown are example and other means of establishing a communications link between the computers can be used.

When used in either a LAN or WAN networking environment, the computer 1202 can access cloud storage systems or other network-based storage systems in addition to, or in place of, external storage devices 1216 as described above, such as but not limited to a network virtual machine providing one or more aspects of storage or processing of information. Generally, a connection between the computer 1202 and a cloud storage system can be established over a LAN 1254 or WAN 1256 e.g., by the adapter 1258 or modem 1260, respectively. Upon connecting the computer 1202 to an associated cloud storage system, the external storage interface 1226 can, with the aid of the adapter 1258 or modem 1260, manage storage provided by the cloud storage system as it would other types of external storage. For instance, the external storage interface 1226 can be configured to provide access to cloud storage sources as if those sources were physically connected to the computer 1202.

The computer 1202 can be operable to communicate with any wireless devices or entities operatively disposed in wireless communication, e.g., a printer, scanner, desktop or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

FIG. 13 is a schematic block diagram of a sample computing environment 1300 with which the disclosed subject matter can interact. The sample computing environment 1300 includes one or more client(s) 1310. The client(s) 1310 can be hardware or software (e.g., threads, processes, computing devices). The sample computing environment 1300 also includes one or more server(s) 1330. The server(s) 1330 can also be hardware or software (e.g., threads, processes, computing devices). The servers 1330 can house threads to perform transformations by employing one or more embodiments as described herein, for example. One possible communication between a client 1310 and a server 1330 can be in the form of a data packet adapted to be transmitted between two or more computer processes. The sample computing environment 1300 includes a communication framework 1350 that can be employed to facilitate communications between the client(s) 1310 and the server(s) 1330. The client(s) 1310 are operably connected to one or more client data store(s) 1320 that can be employed to store information local to the client(s) 1310. Similarly, the server(s) 1330 are operably connected to one or more server data store(s) 1340 that can be employed to store information local to the servers 1330.

Various embodiments may be a system, a method, an apparatus or a computer program product at any possible technical detail level of integration. The computer program product can include a computer readable storage medium (or media) having computer readable program instructions thereon for causing a processor to carry out aspects of various embodiments. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a solid state drive such as M.2 (including non-volatile memory express (NVMe) or serial advanced technology attachment (SATA)), a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network or a wireless network. The network can comprise copper transmission cables, optical transmission fibers, wireless transmission, routers, firewalls, switches, gateway computers or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of various embodiments can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform various aspects.

Various aspects are described herein with reference to flowchart illustrations or block diagrams of methods, apparatus (systems), and computer program products according to various embodiments. It will be understood that each block of the flowchart illustrations or block diagrams, and combinations of blocks in the flowchart illustrations or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart or block diagram block or blocks. These computer readable program instructions can also be stored in a computer readable storage medium that can direct a computer, a programmable data processing apparatus, or other devices to function in a particular manner, such that the computer readable storage medium having instructions stored therein comprises an article of manufacture including instructions which implement aspects of the function/act specified in the flowchart or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart or block diagram block or blocks.

The flowcharts and block diagrams in the Figures illustrate the architecture, functionality, and operation of possible implementations of systems, methods, and computer program products according to various embodiments. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams or flowchart illustration, and combinations of blocks in the block diagrams or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer or computers, those skilled in the art will recognize that this disclosure also can or can be implemented in combination with other program modules. Generally, program modules include routines, programs, components, data structures, etc. that perform particular tasks or implement particular abstract data types. Moreover, those skilled in the art will appreciate that various aspects can be practiced with other computer system configurations, including single-processor or multi-processor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, or a computer. By way of illustration, both an application running on a server and the server can be a component. One or more components can reside within a process or thread of execution and a component can be localized on one computer or distributed between two or more computers. In another example, respective components can execute from various computer readable media having various data structures stored thereon. The components can communicate via local or remote processes such as in accordance with a signal having one or more data packets (e.g., data from one component interacting with another component in a local system, distributed system, or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations.

That is, if X employs A; X employs B; or X employs both A and B, then "X employs A or B" is satisfied under any of the foregoing instances. As used herein, the term "and/or" is intended to have the same meaning as "or." Moreover, articles "a" and "an" as used in the subject specification and annexed drawings should generally be construed to mean "one or more" unless specified otherwise or clear from context to be directed to a singular form. As used herein, the terms "example" or "exemplary" are utilized to mean serving as an example, instance, or illustration. For the avoidance of doubt, the subject matter disclosed herein is not limited by such examples. In addition, any aspect or design described herein as an "example" or "exemplary" is not necessarily to be construed as preferred or advantageous over other aspects or designs, nor is it meant to preclude equivalent exemplary structures and techniques known to those of ordinary skill in the art.

The herein disclosure describes non-limiting examples. For case of description or explanation, various portions of the herein disclosure utilize the term "each," "every," or "all" when discussing various examples. Such usages of the term "each," "every," or "all" are non-limiting. In other words, when the herein disclosure provides a description that is applied to "each," "every," or "all" of some particular object or component, it should be understood that this is a non-limiting example, and it should be further understood that, in various other examples, it can be the case that such description applies to fewer than "each," "every," or "all" of that particular object or component.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:

a processor that executes computer-executable components stored in a non-transitory computer-readable memory, wherein the computer-executable components comprise:

an access component that accesses a medical image on which a first artificial neural network has been executed;

a synthesis component that:

trains a second artificial neural network on the medical image to perform image synthesis; and generates, via execution of the second artificial neural network post-training, a set of synthetic variants of the medical image; and a fine-tune component that instructs a computerized device to fine-tune the first artificial neural network using at least some of the set of synthetic variants of the medical image rather than using the medical image.

2. The system of claim 1, wherein the second artificial neural network is: a generator of a single-image generative adversarial network; a single image denoising diffusion model; or a variational autoencoder.

3. The system of claim 1, wherein the medical image depicts a target anatomical structure, and wherein the computer-executable components further comprise:

a filter component that:

identifies, within the set of synthetic variants of the medical image and via execution of a third artificial neural network that is trained to classify or detect anatomical structures in inputted images, one or more synthetic variants of the medical image that do not depict the target anatomical structure; and removes those one or more synthetic variants of the medical image from the set of synthetic variants of the medical image, such that those one or more synthetic variants of the medical image are not used to fine-tune the first artificial neural network.

4. The system of claim 1, wherein the medical image corresponds to an embedding, and wherein the computer-executable components further comprise:
  a filter component that:
    identifies, within the set of synthetic variants of the medical image and via execution of a third artificial neural network that is trained to create embeddings for inputted images, one or more synthetic variants of the medical image whose embeddings differ by less than a first threshold margin from the embedding of the medical image or by more than a second threshold margin from the embedding of the medical image, wherein the first threshold margin is less than the second threshold margin; and
    removes those one or more synthetic variants of the medical image from the set of synthetic variants of the medical image, such that those one or more synthetic variants of the medical image are not used to fine-tune the first artificial neural network.

5. The system of claim 1, wherein execution of the first artificial neural network on the medical image caused the first artificial neural network to produce a first inferencing task result for the medical image, and wherein the computer-executable components further comprise:
  a filter component that:
    generates, via execution of the first artificial neural network, a set of inferencing task results respectively corresponding to the set of synthetic variants of the medical image;
    identifies, within the set of synthetic variants of the medical image, one or more synthetic variants of the medical image whose inferencing task results differ by more than a threshold margin from the first inferencing task result; and
    removes those one or more synthetic variants of the medical image from the set of synthetic variants of the medical image, such that those one or more synthetic variants of the medical image are not used to fine-tune the first artificial neural network.

6. The system of claim 1, wherein execution of the first artificial neural network on the medical image caused the first artificial neural network to produce a first hidden activation map for the medical image, and wherein the computer-executable components further comprise:
  a filter component that:
    generates, via execution of the first artificial neural network, a set of hidden activation maps respectively corresponding to the set of synthetic variants of the medical image;
    identifies, within the set of synthetic variants of the medical image, one or more synthetic variants of the medical image whose hidden activation maps differ by more than a threshold margin from the first hidden activation map; and
    removes those one or more synthetic variants of the medical image from the set of synthetic variants of the medical image, such that those one or more synthetic variants of the medical image are not used to fine-tune the first artificial neural network.

7. The system of claim 1, wherein the second artificial neural network is configured to synthesize a region of interest within the medical image rather than an entirety of the medical image.

8. The system of claim 1, wherein a training loss of the second artificial neural network is based on: anatomical structure filtration; embedding filtration; inferencing task result filtration; or hidden activation map filtration.

9. A computer-implemented method, comprising:
  accessing, by at least one of one or more devices operatively coupled to a processor, a medical image on which a first artificial neural network has been executed;
  training, by at least one of the one or more devices, a second artificial neural network on the medical image to perform image synthesis;
  generating, by at least one of the one or more devices and via execution of the second artificial neural network post-training, a set of synthetic variants of the medical image; and
  instructing, by at least one of the one or more devices, a computerized device to fine-tune the first artificial neural network using at least some of the set of synthetic variants of the medical image rather than using the medical image.

10. The computer-implemented method of claim 9, wherein the second artificial neural network is: a generator of a single-image generative adversarial network; a single image denoising diffusion model; or a variational autoencoder.

11. The computer-implemented method of claim 9, wherein the medical image depicts a target anatomical structure, and further comprising:
  identifying, by at least one of the one or more devices, within the set of synthetic variants of the medical image, and via execution of a third artificial neural network that is trained to classify or detect anatomical structures in inputted images, one or more synthetic variants of the medical image that do not depict the target anatomical structure; and
  removing, by at least one of the one or more devices, those one or more synthetic variants of the medical image from the set of synthetic variants of the medical image, such that those one or more synthetic variants of the medical image are not used to fine-tune the first artificial neural network.

12. The computer-implemented method of claim 9, wherein the medical image corresponds to an embedding, and further comprising:
  identifying, by at least one of the one or more devices, within the set of synthetic variants of the medical image, and via execution of a third artificial neural network that is trained to create embeddings for inputted images, one or more synthetic variants of the medical image whose embeddings differ by less than a first threshold margin from the embedding of the medical image or by more than a second threshold margin from the embedding of the medical image, wherein the first threshold margin is less than the second threshold margin; and
  removing, by at least one of the one or more devices, those one or more synthetic variants of the medical image from the set of synthetic variants of the medical image, such that those one or more synthetic variants of the medical image are not used to fine-tune the first artificial neural network.

13. The computer-implemented method of claim 9, wherein execution of the first artificial neural network on the medical image caused the first artificial neural network to produce a first inferencing task result for the medical image, and further comprising:

generating, by at least one of the one or more devices and via execution of the first artificial neural network, a set of inferencing task results respectively corresponding to the set of synthetic variants of the medical image;

identifying, by at least one of the one or more devices and within the set of synthetic variants of the medical image, one or more synthetic variants of the medical image whose inferencing task results differ by more than a threshold margin from the first inferencing task result; and removing, by at least one of the one or more devices, those one or more synthetic variants of the medical image from the set of synthetic variants of the medical image, such that those one or more synthetic variants of the medical image are not used to fine-tune the first artificial neural network.

14. The computer-implemented method of claim 9, wherein execution of the first artificial neural network on the medical image caused the first artificial neural network to produce a first hidden activation map for the medical image, and further comprising:

generating, by at least one of the one or more devices and via execution of the first artificial neural network, a set of hidden activation maps respectively corresponding to the set of synthetic variants of the medical image;

identifying, by at least one of the one or more devices and within the set of synthetic variants of the medical image, one or more synthetic variants of the medical image whose hidden activation maps differ by more than a threshold margin from the first hidden activation map; and removing, by at least one of the one or more devices, those one or more synthetic variants of the medical image from the set of synthetic variants of the medical image, such that those one or more synthetic variants of the medical image are not used to fine-tune the first artificial neural network.

15. The computer-implemented method of claim 9, wherein the second artificial neural network is configured to synthesize a region of interest within the medical image rather than an entirety of the medical image.

16. The computer-implemented method of claim 9, wherein a training loss of the second artificial neural network is based on: anatomical structure filtration; embedding filtration; inferencing task result filtration; or hidden activation map filtration.

17. A computer program product for facilitating medical image privacy preservation via image synthesis and filtration, the computer program product comprising a non-transitory computer-readable memory having program instructions embodied therewith, the program instructions executable by a processor to cause the processor to:

access a privacy-restricted medical image which a clinical machine learning model has analyzed;

generate, via execution of a generative model that is trained on the privacy-restricted medical image to perform image synthesis, a set of unrestricted synthetic variants of the privacy-restricted medical image; and re-train the clinical machine learning model using at least some of the set of unrestricted synthetic variants instead of the privacy-restricted medical image.

18. The computer program product of claim 17, wherein the generative model is: a generator of a single-image generative adversarial network; a single image denoising diffusion model; or a variational autoencoder.

19. The computer program product of claim 17, wherein the program instructions are further executable to cause the processor to:

filter out of the set of unrestricted synthetic variants any variants that:

do not depict a same anatomical structure as the privacy-restricted medical image;

correspond to embeddings that are excessively similar to or excessively dissimilar from an embedding of the privacy-restricted medical image;

correspond to inferencing task results that do not match an inferencing task result produced by the clinical machine learning model for the privacy-restricted medical image; or correspond to hidden activation maps that are excessively dissimilar from a hidden activation map produced by the clinical machine learning model for the privacy-restricted medical image.

20. The computer program product of claim 17, wherein the generative model is configured to synthesize a region of interest within the privacy-restricted medical image rather than an entirety of the privacy-restricted medical image.

* * * * *